United States Patent
Cruz et al.

(10) Patent No.: US 11,951,124 B2
(45) Date of Patent: Apr. 9, 2024

(54) TELLURIUM NANOWIRES WITH ANTICANCER PROPERTIES SYNTHESIZED BY GREEN CHEMISTRY

(71) Applicant: Northeastern University, Boston, MA (US)

(72) Inventors: David Medina Cruz, Jamaica Plain, MA (US); Ada Vernet Crua, Brighton, MA (US); Thomas J. Webster, Barrington, RI (US)

(73) Assignee: Northeastern University, Boston, MA (US)

( * ) Notice: Subject to any disclaimer, the term of this patent is extended or adjusted under 35 U.S.C. 154(b) by 310 days.

(21) Appl. No.: 16/735,009

(22) Filed: Jan. 6, 2020

(65) Prior Publication Data

US 2020/0215101 A1    Jul. 9, 2020

Related U.S. Application Data

(60) Provisional application No. 62/788,344, filed on Jan. 4, 2019.

(51) Int. Cl.
| | | |
|---|---|---|
| *A61K 33/00* | (2006.01) | |
| *A61K 9/51* | (2006.01) | |
| *A61P 35/00* | (2006.01) | |
| *B82Y 5/00* | (2011.01) | |

(52) U.S. Cl.
CPC ............ *A61K 33/00* (2013.01); *A61K 9/5146* (2013.01); *A61K 9/5161* (2013.01); *A61P 35/00* (2018.01); *B82Y 5/00* (2013.01)

(58) Field of Classification Search
None
See application file for complete search history.

(56) References Cited

PUBLICATIONS

Lu et al. (Langmuir 2005, 21, 6002-6005) A Green Chemical Approach to the Synthesis of Tellurium Nanowires.*
Wang et al., "The Antimicrobial Activity of Nanoparticles: Present Situation and Prospects for the Future." International Journal of Nanomedicine vol. 12 (2017): 1227-1249.
Hemeg, Hassan "Nanomaterials for Alternative Antibacterial Therapy." International Journal of Nanomedicine vol. 12 (2017): 8211-8225.
Graves et al., "Antimicrobial Nanomaterials: Why Evolution Matters." Nanomaterials (Basel, Switzerland) 7.10 (2017): 10 pages.
Kulkarni et al., "Biosynthesis of Metal Nanoparticles: A Review." Journal of Nanotechnology 2014 (2014): 1-8.
Al et al., "Nanotoxicology and Nanoparticle Safety in Biomedical Designs." International journal of nanomedicine 6 (2011): 1117-27.
Shah et al., "Green Synthesis of Metallic Nanoparticles via Biological Entities." Materials 8.11 (2015): 7278-7308.
Cruz et al., "Synthesis and Characterization of Biogenic Selenium Nanoparticles with Antimicrobial Properties Made by *Staphylococcus aureus*, Methicillin-Resistant *Staphylococcus aureus* (MRSA), *Escherichia coli*, and Pseudomonas Aeruginosa." Journal of Biomedical Materials Research Part A 106.5 (2018): 1400-1412.
Molnar et al., "Green Synthesis of Gold Nanoparticles by Thermophilic Filamentous Fungi." Scientific Reports 8.1 (2018): 12 pages.
Makarov et al., "Green Nanotechnologies: Synthesis of Metal Nanoparticles Using Plants." Acta naturae 6.1 (2014): 35-44.
Singh et al., "Biological Synthesis of Nanoparticles from Plants and Microorganisms." Trends in Biotechnology 34.7 (2016): 12 pages.
Gurunathan et al., "A Green Chemistry Approach for Synthesizing Biocompatible Gold Nanoparticles." Nanoscale Research Letters 9:248 (2014): 11 pages.
Rehana et al., "Evaluation of Antioxidant and Anticancer Activity of Copper Oxide Nanoparticles Synthesized Using Medicinally Important Plant Extracts." Biomedicine & Pharmacotherapy 89 (2017): 1067-1077.
Kelkawi et al., "Green Synthesis of Silver Nanoparticles Using Mentha Pulegium and Investigation of Their Antibacterial, Antifungal and Anticancer Activity." IET Nanobiotechnology 11.4 (2017): 370-376.
Hussain et al., "Green synthesis of nanoparticles and its potential application", Biotechnol. Lett. (2016) 38:545-560, doi: 10.1007/s10529-015-2026-7.
Larios-Rodriguez et al., "Bio-synthesis of gold nanoparticles by human epithelial cells, in vivo", Nanotechnology 22 (2011) 355601 (8pp).
El-Said et al., "Synthesis of Metal Nanoparticles Inside Living Human Cells Based on the Intracellular Formation Pocess", Advanced Materials, 2014, 26, 910-918.
Dhand et al., "Green synthesis of silver nanoparticles using Coffea arabica seed extract and its antibacterial activity", Materials Science and Engineering C 58 (2016) 36-43.
Mukherjee et al., "Green chemistry approach for the synthesis and stabilization of biocompatible gold nanoparticles and their potential applicatios in cancer therapy", Nanotechnology 23 (2012) 455103 (13pp).
Sudhasree et al., "Synthesis of nickel nanoparticles by chemical and green route and their comparison in respect to biological effect and toxicity", Toxicological & Environmental Chemistry, vol. 96, No. 5, 743-754 (2014).
Hong et al., "Facile synthesis of PdAgTe nanowires with superior electrocatalytic activity", Journal of Power Sources, 272 (2014) 940-945.
Sredni, Benjamin "Immunomodulating tellurium compounds as anti-cancer agents", Seminars in Cancer Biology, 22 (2012) 60-69.

* cited by examiner

*Primary Examiner* — Tigabu Kassa
(74) *Attorney, Agent, or Firm* — Verrill Dana, LLP

(57) ABSTRACT

Tellurium nanowires synthesized using green chemistry methods and having unique morphologies and functional properties are provided. The nanowires have a core of hexagonal crystal phase tellurium and a polymer coating, and can be used for treating cancer without apparent cytotoxicity toward normal human cells.

7 Claims, 25 Drawing Sheets

TELLURIUM NANOWIRES WITH ANTICANCER PROPERTIES SYNTHESIZED BY GREEN CHEMISTRY

CROSS-REFERENCE TO RELATED APPLICATIONS

This application claims priority to U.S. Provisional Application No. 62/788,344 filed 4 Jan. 2019, the entirety of which is incorporated herein by reference.

BACKGROUND

In a world where the population density increases and natural resources disappear, there are concerns that arise from the increased use of synthetic chemicals. [1, 2, 3]. This is especially true for nanotechnology, which produces materials at a small scale, often with novel properties much different from bulk materials. In recent years, the increased implementation of nanotechnology has provided solutions for specific problems including antimicrobial resistance [4, 5, 6], cancer treatments [7, 8], bio-imaging [9, 10, 11], and drug delivery [12, 13, 14]. Traditional physicochemical approaches for the synthesis of nanomaterials involve easy and straightforward protocols, using available techniques such as laser ablation [15, 16] or chemical vapor deposition [17,18]. Nevertheless, there is a cost associated with chemical synthetic methods, such as the production of toxic byproducts, the use of harsh chemicals, and lack of biocompatibility. Therefore, new synthesis methods are needed, and green chemistry can offer a suitable solution, with safe and environmentally friendly design, manufacture, and use of chemical products that do not involve toxic or harsh by-products [19, 20].

Green chemistry is considered an alternative approach in that it combines materials derived from synthetic chemistry and from nature to address problems of traditional synthesis. Green chemistry approaches are especially useful for the generation of metallic nanoparticles, which are nanoscale structures that can address concerns in both healthcare and industrial applications [21, 22, 23]. Therefore, green chemistry approaches offer the chance to use living organisms (such as bacteria [24], human cells [25, 26], fungi [27], or plants [28, 29]) as well as dietary and organic natural compounds (such as coffee [30], tea or honey extracts [31]) or biological waste material produced from industrial alimentary plants [32], to naturally synthesize nanostructures. These nanostructures can show antibacterial and/or anticancer properties and can be used as drug delivery carriers and in industrial applications. Green chemistry approaches are cost effective, environmentally friendly, and employ standard reaction parameters in redox-reduction or hydrothermal techniques to generate specifically metallic nanostructures with high throughput.

SUMMARY

Green chemistry methods for synthesis of tellurium nanowires are provided. Tellurium nanowires synthesized using the green chemistry methods have, for example, novel cytocompatibility, chemical, and anticancer properties. The green chemistry synthetic methods can utilize starch with an easy and straightforward hydrothermal method. The resulting tellurium nanowires are characterized herein using transmission electron microscopy, scanning electron microscopy, energy-dispersive X-ray spectroscopy, Fourier-transform infrared spectroscopy, X-ray powder diffraction, X-ray photoelectron spectroscopy, and optical microscopy for morphology, size, and chemical composition. The resulting "green" tellurium (Te) nanowires were tested in cytotoxicity tests with human dermal fibroblasts and human melanoma cells (to assess anticancer properties). The results showed that a treatment with the green chemistry synthesized Te nanowires at concentrations between 5 and 100 µg/mL improved the proliferation of healthy cells and decreased cancerous cell growth over a 5-day period. Importantly, the green chemistry synthesized Te nanowires (GREEN-TeNWs) outperformed those produced by traditional synthetic chemical methods. The GREEN-TeNWs can have, for example, no nitrogen while having unique coatings and morphologies (e.g., star-shaped nanostructures). The green chemistry approaches herein can provide nanoscale structures that can effectively and efficiently address concerns in both healthcare and industrial applications without the production of toxic byproducts, without the use of harsh chemicals, and without lack of biocompatibility in the green nanomaterials.

The Te nanowires can be part of nanostructures that can include more than one nanowire. The nanoscale Te structures described herein can provide treatments for cancer, infections, and other diseases. As used herein, the term "nanostructure" refers to a structure having at least one dimension on the nanoscale, that is, at least on dimension between about 0.1 and 100 nm. Nanostructures can include, but are not limited to, nanowires, nanotubes, nanoparticles (e.g., hexagonal or triangular shaped nanoparticles), nanospheres, star-shaped nanostructures, nano-radiating structures, and combinations thereof. Star-shaped nanostructures may contain a plurality of nanowires. A nanowire may contain a wire having a diameter on the nanoscale with a length on the micro or millimeter scale.

The present technology includes a method of inhibiting the proliferation of cancer cells in a subject, such as a human or other mammalian subject. The method includes administering GREEN tellurium nanowires to the subject. The coated tellurium nanowires have a core comprising tellurium and can optionally also contain an outer coating or sheath that includes or is composed essentially of a polymer. When the nanowires are administered to the subject, proliferation of the cancer cells is inhibited. The nanowires can be formulated and administered by any known method suitable for allowing them to access the cancer cells within the body of the subject, such as by intravenous injection of a suspension of the nanowires in saline, or implantation of solid formulated or suspension formulated nanowires into a solid tumor. The administration of the GREEN tellurium nanowires can inhibit the proliferation of cancer cells preferentially over inhibition of proliferation of non-cancer cells in the subject. Preferably, the proliferation of cancer cells is inhibited at least twice as much as proliferation of non-cancerous cells is inhibited in the subject The polymer used to coat the tellurium nanowires can be a biopolymer isolated from a naturally occurring biological material, and optionally modified, such as by cross-linking, heat treatment, or chemical modification. For example, the polymer can be starch, or cross-linked starch, or starch modified by heat treatment, such as gelatinized starch. The polymer also can be a synthetic polymer, which is preferably non-toxic and biodegradable, such as polyethylene glycol. The core of the nanowires contains or consists essentially of tellurium hexagonal crystal structure; preferably, the core does not contain comprise amorphous tellurium. The coated tellurium nanowires can be present as individual, non-associated nanowires, or at least a portion of the nanowires can have a star-shaped structure comprising coated tellurium nanowires radiating outwards from a central point, where the nanowires are clustered together. The coated tellurium nanowires can have a diameter of about 15 nm to about 35 nm and the polymer coating, such as a starch coating, can be at least 1 nm thick.

The present technology also provides a method of producing coated tellurium nanowires. The method includes the following steps: (a) mixing telluric acid ($H_2TeO_4$) with an aqueous polymer solution or suspension to obtain a mixture of telluric acid, polymer, and water; and (b) heating the mixture in a sealed vessel at a temperature from about 120° C. to about 200° C. for about 2 hours to about 20 hours. The mixture is subjected to elevated pressure during step (b) as well as heat. The method optionally can further include: (c) centrifuging the product from step (b) to obtain a pellet; (d) resuspending the pellet in water; and (e) lyophilizing the resuspended pellet to obtain a dry powder containing the nanowires.

DETAILED DESCRIPTION

Described herein are tellurium nanowires synthesized using green chemistry methods, methods of treating diseases (e.g., cancer, infections) utilizing the green-synthesized tellurium nanowires, and green chemistry methods for synthesis of tellurium nanowires. Tellurium nanowires were also synthesized using traditional chemical synthesis, and the properties of the nanowires produced by the green chemistry and the traditional chemical synthetic method were compared. For comparison to traditional chemical synthetic methods, the green synthetic method was a hydrothermal synthesis method that utilized tellurium salt and starch. The traditional synthetic method used metallic Te salt and chemical synthetic, toxic reducing agents such as ammonia and hydrazine. Both methods were similar with respect to later (e.g., isolation and purification) steps and with respect to reaction conditions. After purification, the nanostructures were characterized and compared using transmission electron microscopy (TEM), scanning electron microscopy (SEM), and energy-dispersive X-ray spectroscopy (EDX), for determining morphology, size, and composition. The nanostructures were applied to cancer cells because cancer cells do not have the mechanism to eliminate some metallic structures, unlike normal cells that have this ability, leading to selective cancer cell death while maintaining the viability of healthy cells. Other cells that do not have a mechanism to eliminate or degrade some metallic structures can be bacterial or other infectious cells (e.g., fungal). Cytocompatibility and anticancer properties of the chemically-synthesized tellurium nanowires (CHEM-TeNWs) and green-synthesized tellurium nanowires (GREEN-TeNWs) were compared. Cytotoxicity assays were performed over five days with both human dermal fibroblasts (HDF) cells and human melanoma cancer cells.

Figure 1:
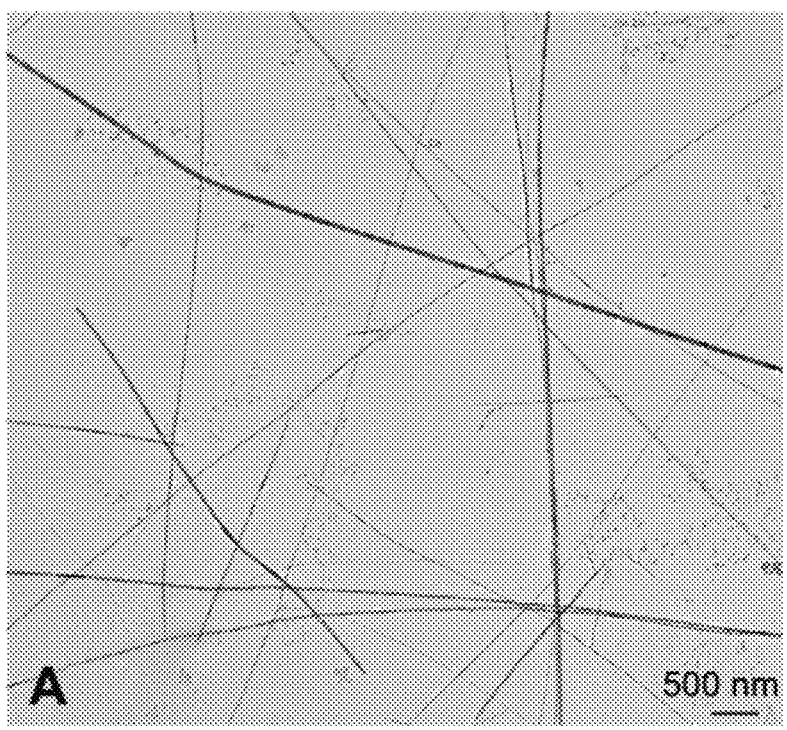
FIG. 1 shows a transmission electron microscopy (TEM) image of chemically synthesized tellurium nanowires (CHEM-TeNWs).
Figure 2:
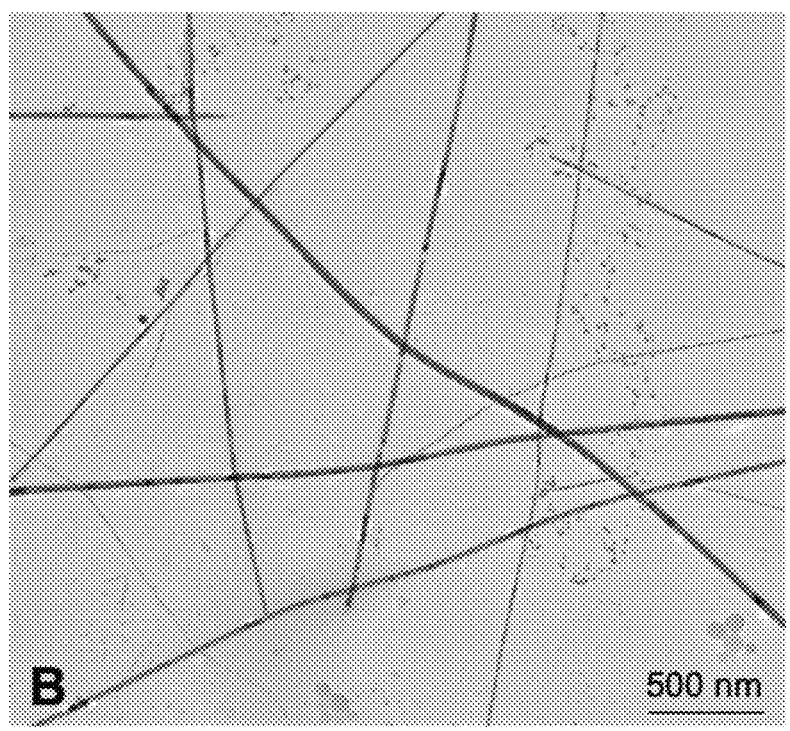
FIG. 2 shows a transmission electron microscopy (TEM) image of chemically synthesized tellurium nanowires (CHEM-TeNWs). Increased magnification is shown in FIG. 2 compared to FIG. 1.
Figure 5:
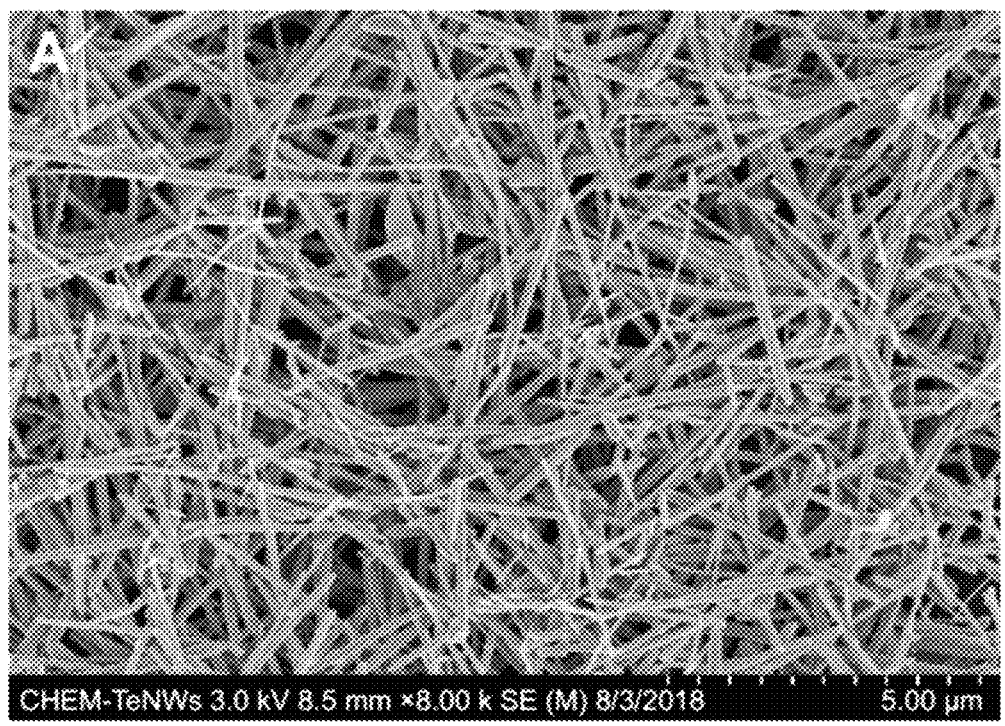
FIG. 5 shows a scanning electron microscopy (SEM) image of chemically synthesized tellurium nanowires (CHEM-TeNWs).
Figure 6:
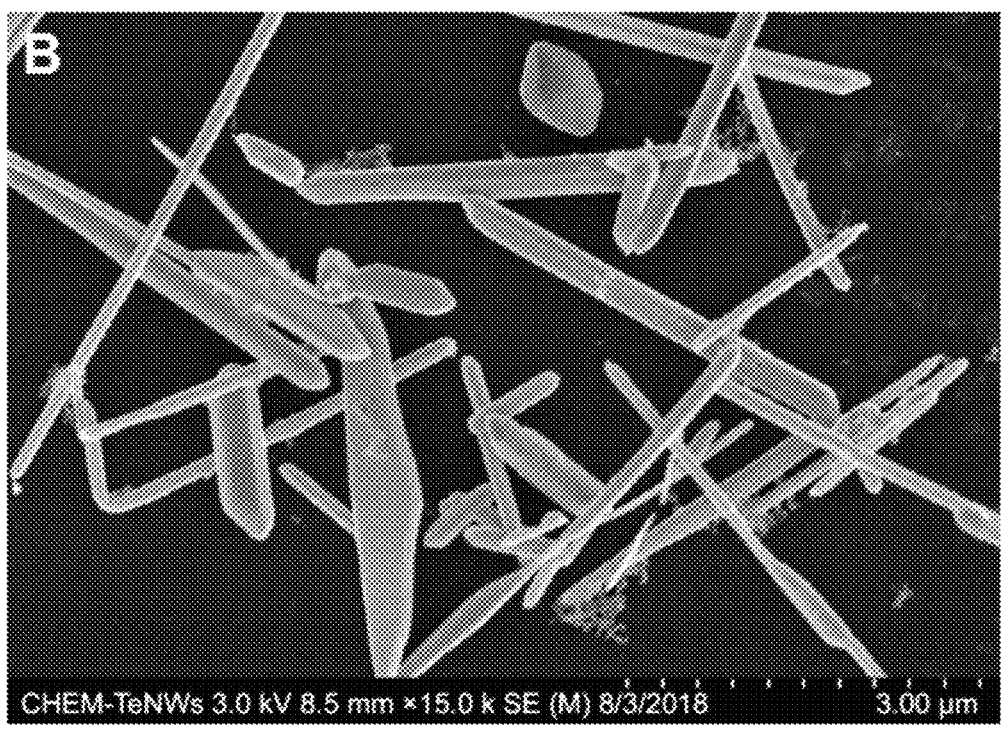
FIG. 6 shows a scanning electron microscopy (SEM) image of chemically synthesized tellurium nanowires (CHEM-TeNWs).

For traditional chemical synthesis of tellurium nanowires, sodium tellurite was mixed with polyvinylpyrrolidone (PVP) and dissolved in deionized water. Next, hydrazine hydrate and $NH_3$ was added. The solution was stirred at room temperature, then transferred into a teflon-lined stainless steel reactor and placed into an oven at 180° C. for 4 hours. After the reaction, the mixture was allowed to cool down at room temperature. The nanowire solution was centrifuged at 10,000 rpm for 20 minutes, and the pellet was subsequently washed twice with water and centrifuged again at the same rate and time. Finally, the precipitate was re-suspended in deionized water, frozen at −80° C. for 4 hours and lyophilized overnight. The final powder was re-suspended in a suitable amount of deionized, sterile water to reach the final concentration needed for further experiments. Transmission electron microscopy (TEM) images of chemically synthesized tellurium nanowires (CHEM-TeNWs) are shown in FIGS. 1-2, and scanning electron microscopy (SEM) images of chemically synthesized tellurium nanowires (CHEM-TeNWs) are shown in FIGS. 5-6.

For a green synthesis route to synthesize tellurium nanowires, telluric acid ($H_2TeO_4$) was mixed and stirred with a starch solution in deionized water. The resulting mixture can be heated in a sealed reaction vessel at a reaction temperature from about 120° C. to about 200° C. for a reaction time period of about 2 to about 20 hours. The starch is believed to reduce the metal, resulting in formation of the nanostructures. For example, the mixture can be transferred to a teflon-lined stainless steel reactor and placed into an oven at about 160° C. for about 15 hours. An experiment was performed using this approach. The mixture was then allowed to cool down to room temperature. The mixture was then centrifuged, washed, and lyophilized in the same way as the CHEM-TeNWs (above). The final powder was re-suspended in a suitable amount of deionized, sterile water to reach the final concentration needed for further experiments.

For the green synthesis, the reaction temperature can be in the range of about 140° C. to about 180° C. The reaction time can be, for example, about 6 to about 18 hours or about 10 to about 18 hours. Centrifugation can be at about 10,000 rpm for about 20 minutes. After centrifugation, the pellet can be washed/rinsed with water and centrifuged again at the same rate and time. Isolation and purification can be done by any means known in the art, and the centrifugation with rinsing is a non-limiting example.

Figure 3:
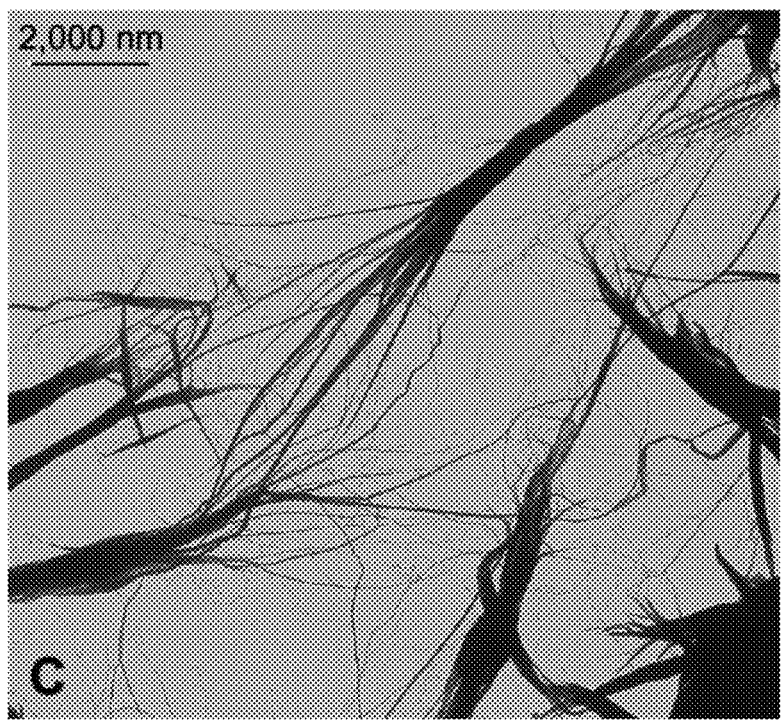
FIG. 3 shows a transmission electron microscopy (TEM) image of green synthesized tellurium nanowires (GREEN-TeNWs).
Figure 4:
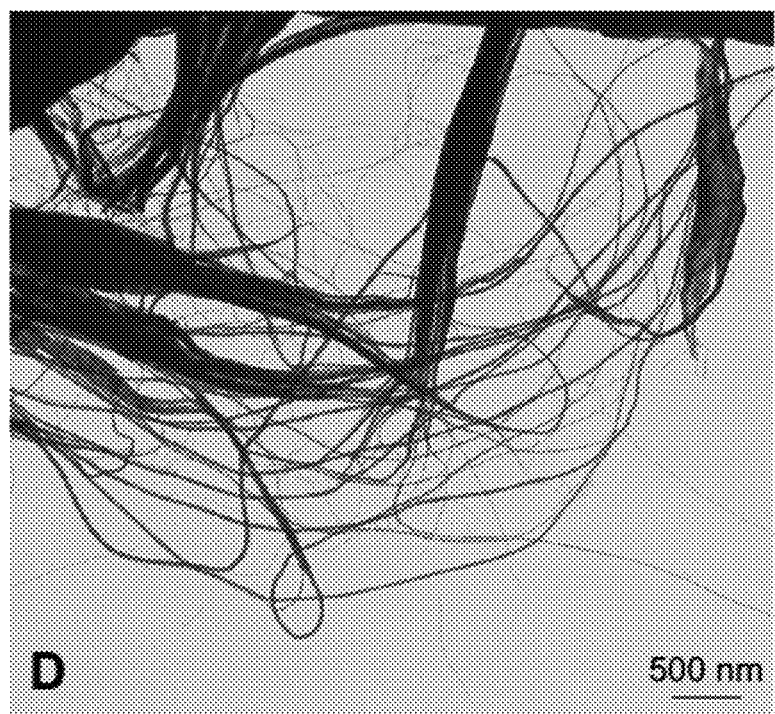
FIG. 4 shows a transmission electron microscopy (TEM) image of green synthesized tellurium nanowires (GREEN-TeNWs). Magnification is increased compared to FIG. 3.
Figure 7:
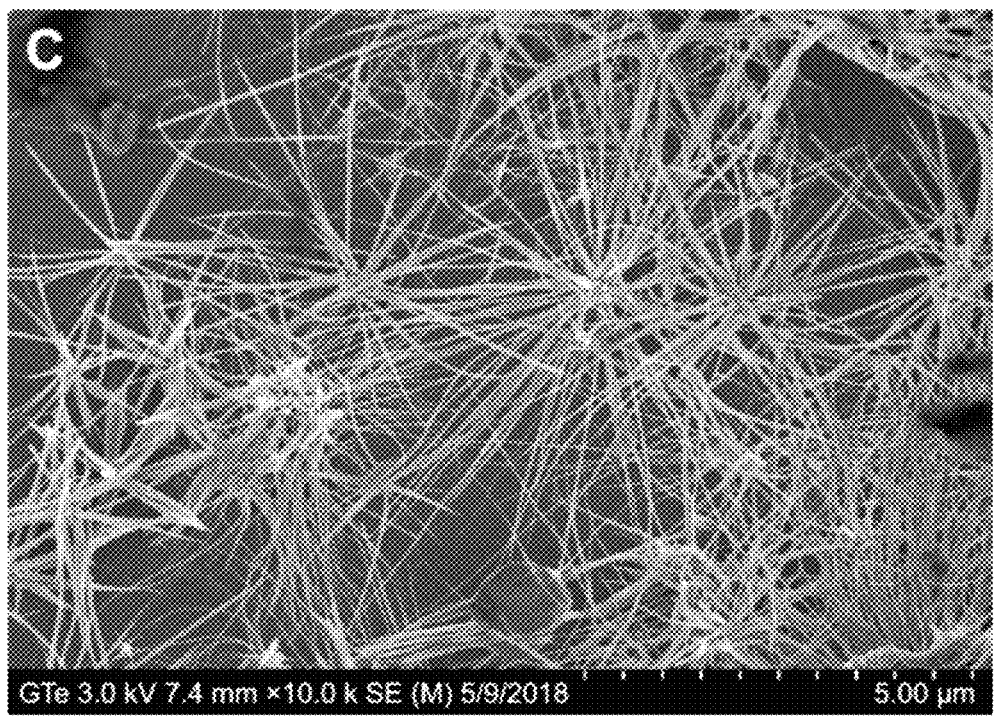
FIG. 7 shows a scanning electron microscopy (SEM) image of green synthesized tellurium nanowires (GREEN-TeNWs).
Figure 8:
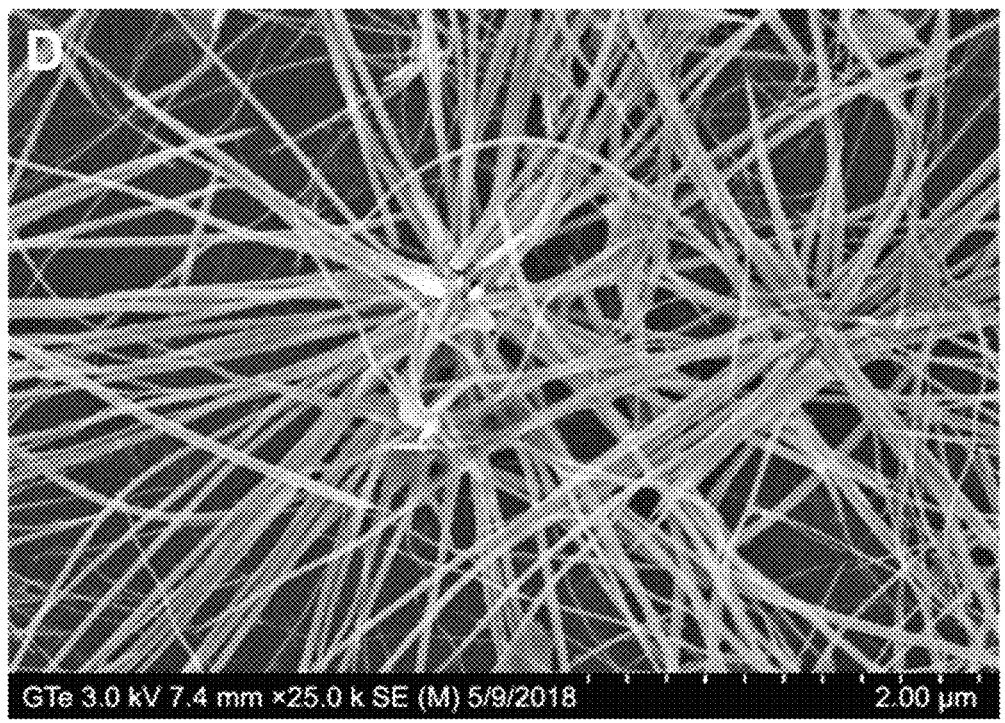
FIG. 8 shows a scanning electron microscopy (SEM) image of green synthesized tellurium nanowires (GREEN-TeNWs).

Transmission electron microscopy (TEM) images of green synthesized tellurium nanowires (GREEN-TeNWs) are shown in FIGS. 3-4, and scanning electron microscopy (SEM) images of GREEN-TeNWs are shown in FIGS. 7-8. As can be seen in FIGS. 7-8, the GREEN-TeNWs show growth initiated from a point with extended growth radiating from the central point. The GREEN-TeNWs grow from a cluster and extend for several micrometers, with a star-shaped uniform structure. The star-shaped uniform nanostructures arise due to the green synthesis, and the GREEN-TeNWs also have a unique coating. The morphology, coating and chemical composition (discussed later) are not observed in the CHEM-TeNWs. The GREEN-TeNWs shown were reacted in a teflon-lined stainless steel reactor at 160° C. for 15 hours. The GREEN-TeNWs were isolated and purified by exactly the same methods as the CHEM-TeNWs, were centrifuged at 10,000 rpm for 20 minutes; the pellet was subsequently washed twice with water and centrifuged again at the same rate and time. The precipitate was re-suspended in deionized water, frozen at −80° C. for 4 hours and lyophilized overnight. The final powder was re-suspended in a suitable amount of deionized, sterile water to reach the final concentration needed for further experiments.

The uniformity of the GREEN-TeNWs' morphology is thought to enhance their action in anticancer and biocompatibility properties in comparison with the chemically synthesized products, along with the coating and chemical composition of the GREEN-TeNWs. Within each star-shaped nanostructure, the total diameter of each of the GREEN-TeNWs was about 25±8 nm, or about 15 to about 35 nm (see Table 5), and each GREEN-TeNW extended for several microns. As demonstrated later, the properties of the GREEN-TeNWs include cancer cell inhibition. A method of inhibiting proliferation of a cancer cell can comprise contacting the cancer cell with GREEN-TeNWs. For example, a concentration of about 5 µL/mL-100 µL/mL, about 10-30 µL/mL GREEN-TeNWs, or about 25 µL/mL GREEN-TeNWs. The $IC_{50}$ of the GREEN-TeNWs for melanoma cells is 16.46±1.96 µg/mL and for HDF cells is 70.05±10.58 µg/mL (Table 6). The GREEN-TeNWs inhibit cancer cell growth more compared to inhibition of non-cancerous cell growth (Example 3, FIG. 22). Methods of inhibiting infectious cells or other cells that do not have a mechanism to eliminate or degrade some metallic structures can also comprise GREEN-TeNWs, for example, by administering an effective amount of GREEN-TeNWs. Tellurium nanowires made according to the green synthesis method can be utilized for a method of treating cancer, the method comprising administering to a subject in need thereof an effective amount of a composition comprising the GREEN-TeNWs.

Figure 9:
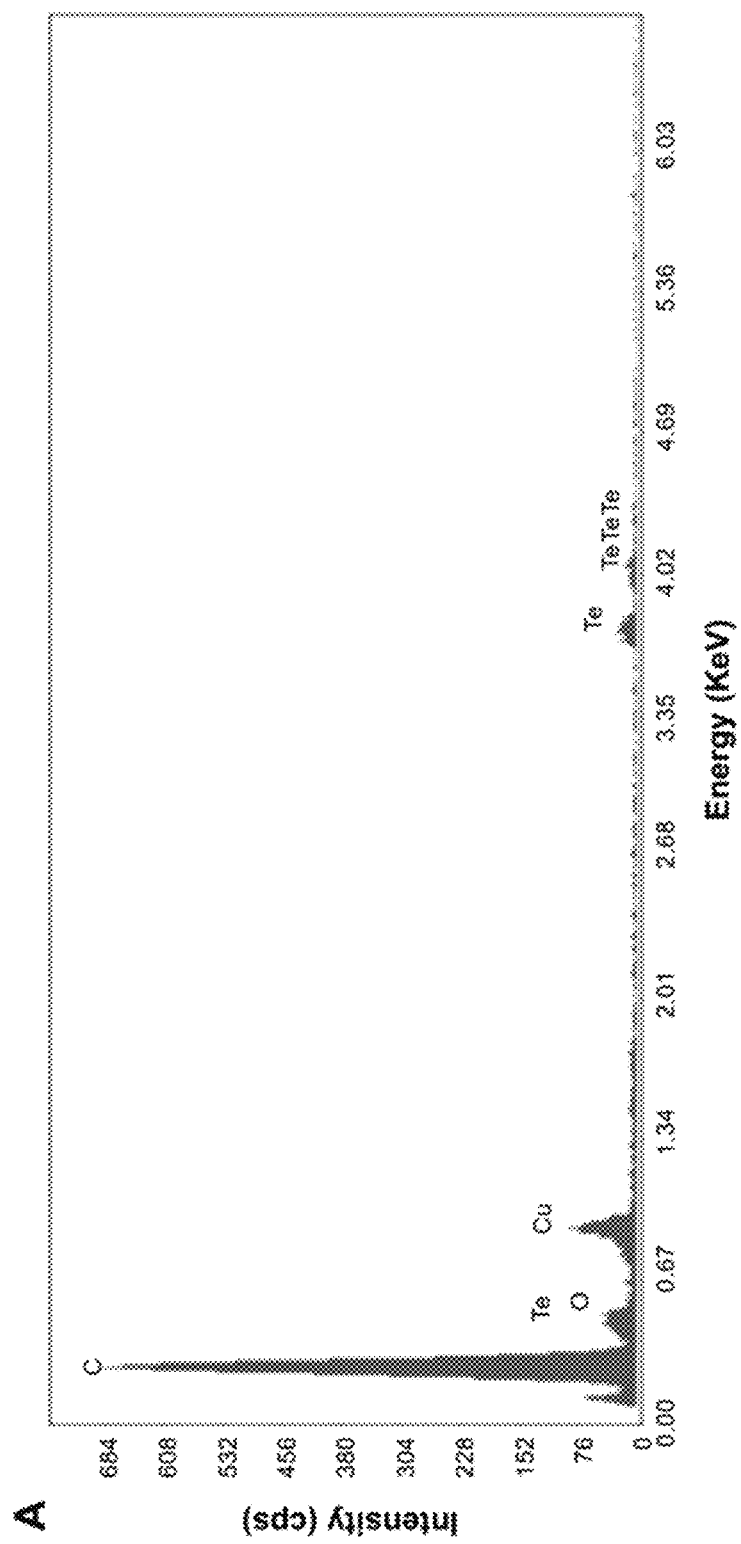
FIG. 9 shows energy-dispersive X-ray of chemically synthesized tellurium nanowires (CHEM-TeNWs).
Figure 10:
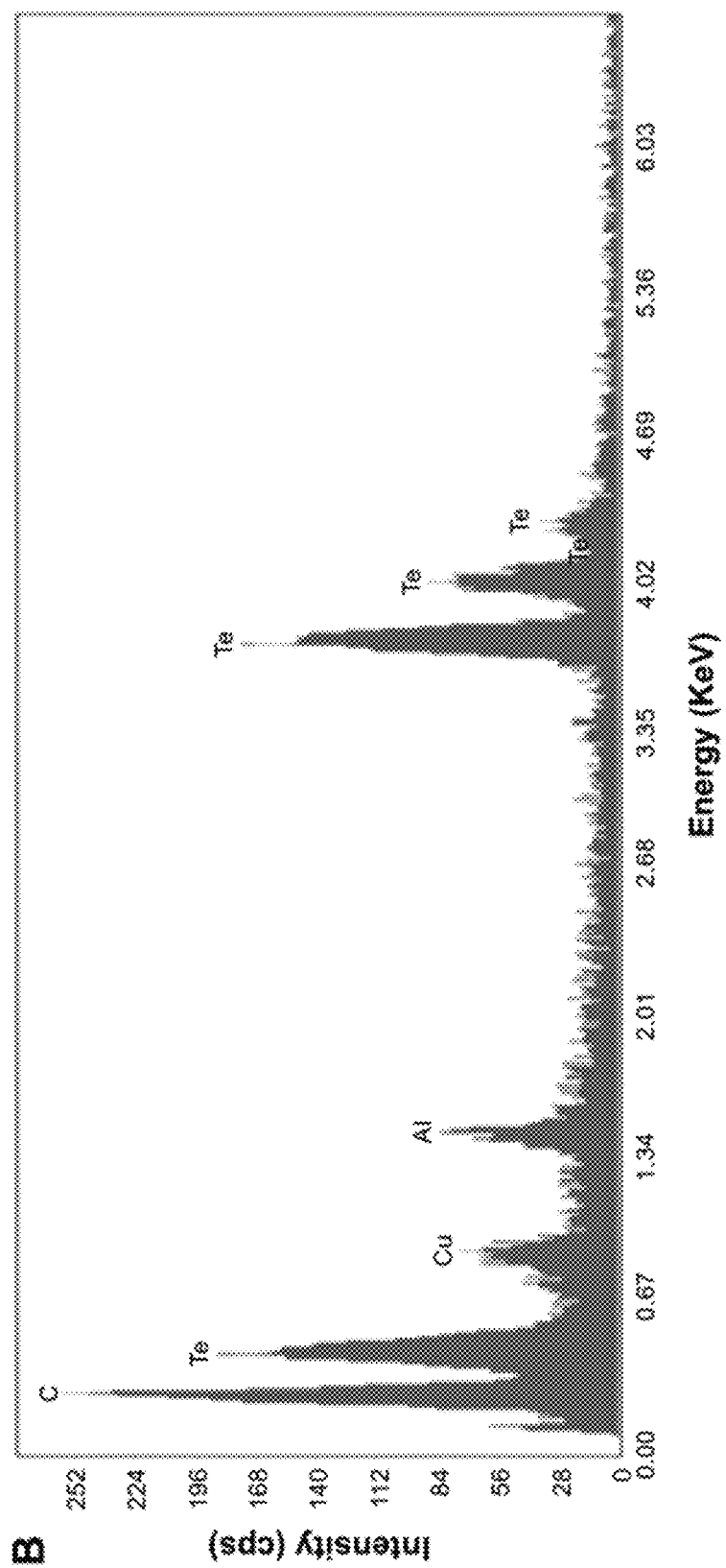
FIG. 10 shows energy-dispersive X-ray of green synthesized tellurium nanowires (GREEN-TeNWs).
Figure 11:
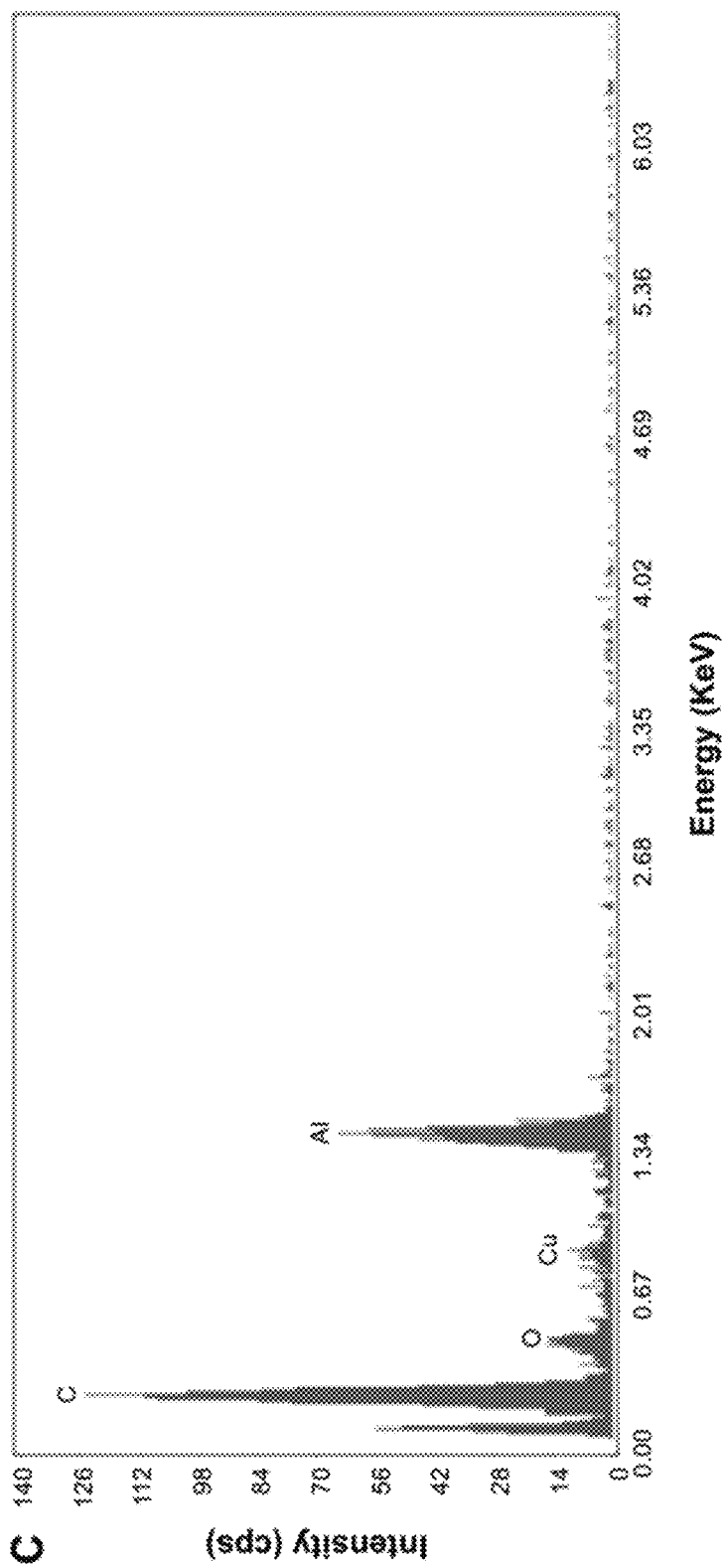
FIG. 11 shows energy-dispersive X-ray of the surrounding coating of green synthesized tellurium nanowires (GREEN-TeNWs).

The SEM images demonstrate dramatically different morphology between the CHEM-TeNWs and GREEN-TeNWs, and further analyses were conducted. EDX spectroscopy for CHEM-TeNWs (FIG. 9) shows that the electron-dense nanowires have specific Te absorption peaks. In comparison, for GREEN-TeNWs (FIG. 10), the peaks for Te are higher due to the higher concentration of Te within. In FIG. 11, EDX spectroscopy on the coating areas of the GREEN-TeNWs shows the carbon peak is significantly raised compared with the measurement of the Te metallic core in FIG. 10. This significant carbon peak, aside from the absence of a Te peak in FIG. 11, indicates an organic composition of the coating of the GREEN-TeNWs.

Figure 12:
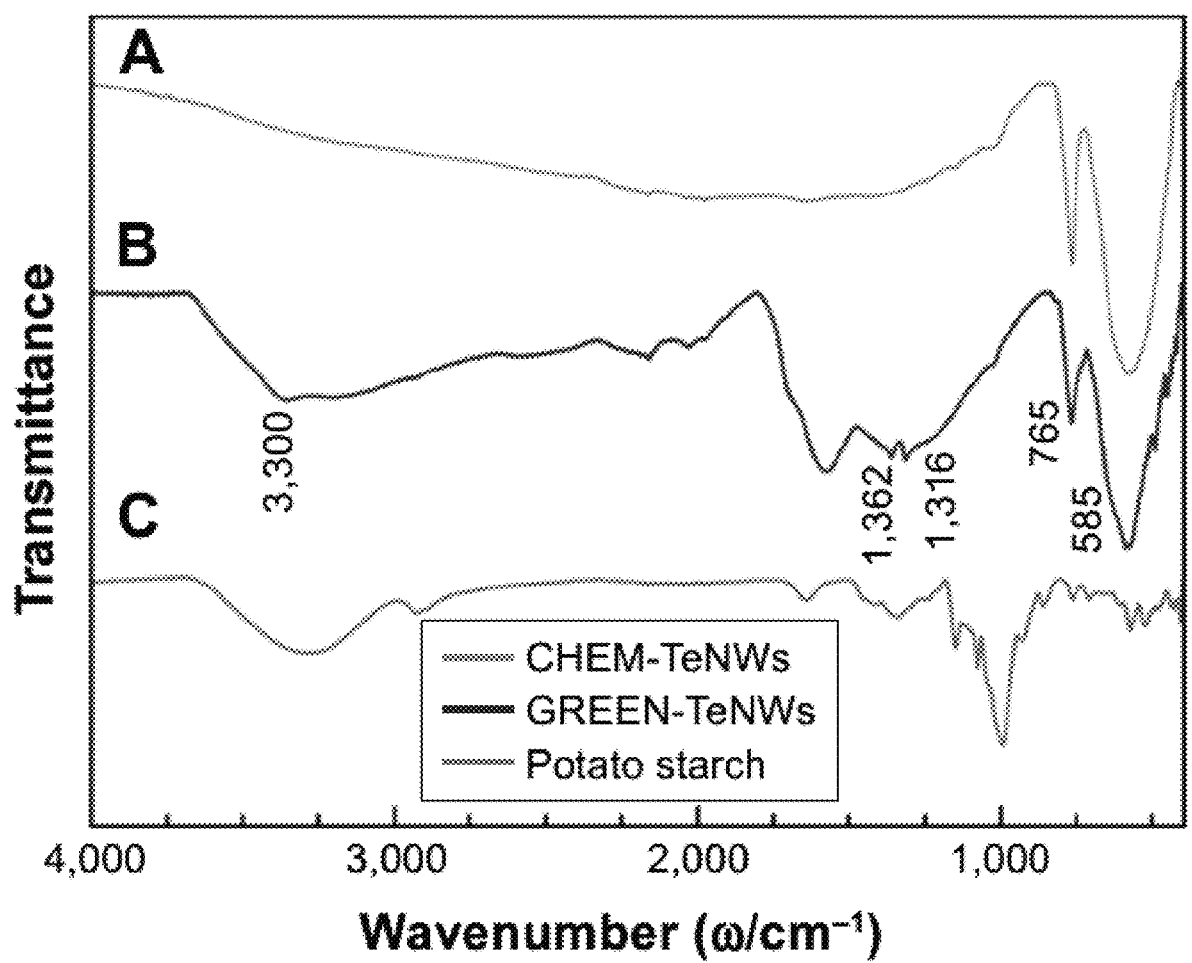
FIG. 12 shows an overlayed comparison of the FT-IR spectra of CHEM-TeNWs (A, top spectrum), GREEN-TeNWs (B, center spectrum), and potato starch (C, bottom spectrum). The IR spectra were acquired in ATR mode.

In FIG. 12, the FT-IR spectra of CHEM-TeNWs, GREEN-TeNWs, and potato starch are compared. The FT-IR spectra in FIG. 12 were acquired in attenuated total reflectance (ATR) mode using 5 µg of dried sample. The depth of penetration of ATR can range from about 0.5 microns up to about 5 microns depending upon experimental conditions, which is a relatively large penetration compared to the diameter of the TeNWs (see Table 5). A more surface sensitive technique, X-ray photoelectron spectroscopy (XPS), which can penetrate about 5-20 Å (0.5-2 nanometers), is also utilized in Table 3 (discussed below), providing further insights into the coating on the GREEN-TeNWs. In the ATR (FT-IR) data, the CHEM-TeNWs and GREEN-TeNWs samples both show absorption bands (see FIG. 12) of Te oxide at around 765 and 585 $cm^{-1}$, which can be related to the symmetrical equatorial and asymmetrical axial stretching frequencies of the Te—O bond, respectively. The FT-IR spectrum of GREEN-TeNWs presents a vibrational band at around 3,300 $cm^{-1}$ related to the O—H stretching mode of starch, and this band is also observed in the potato starch spectrum. The O—H band at around 3,300 is broadened due to H-bonding in the solid (ATR) state. The vibrational bands at the region of 1,300-1,400 $cm^{-1}$ are due to C—O—H bending and $CH_2$ twisting of the starch structure. The bands in the FT-IR spectrum of GREEN-TeNWs are consistent with potato starch. A single layer of starch would be at least about 1 nm thick based on the size of a glucose molecule.

Figure 13:
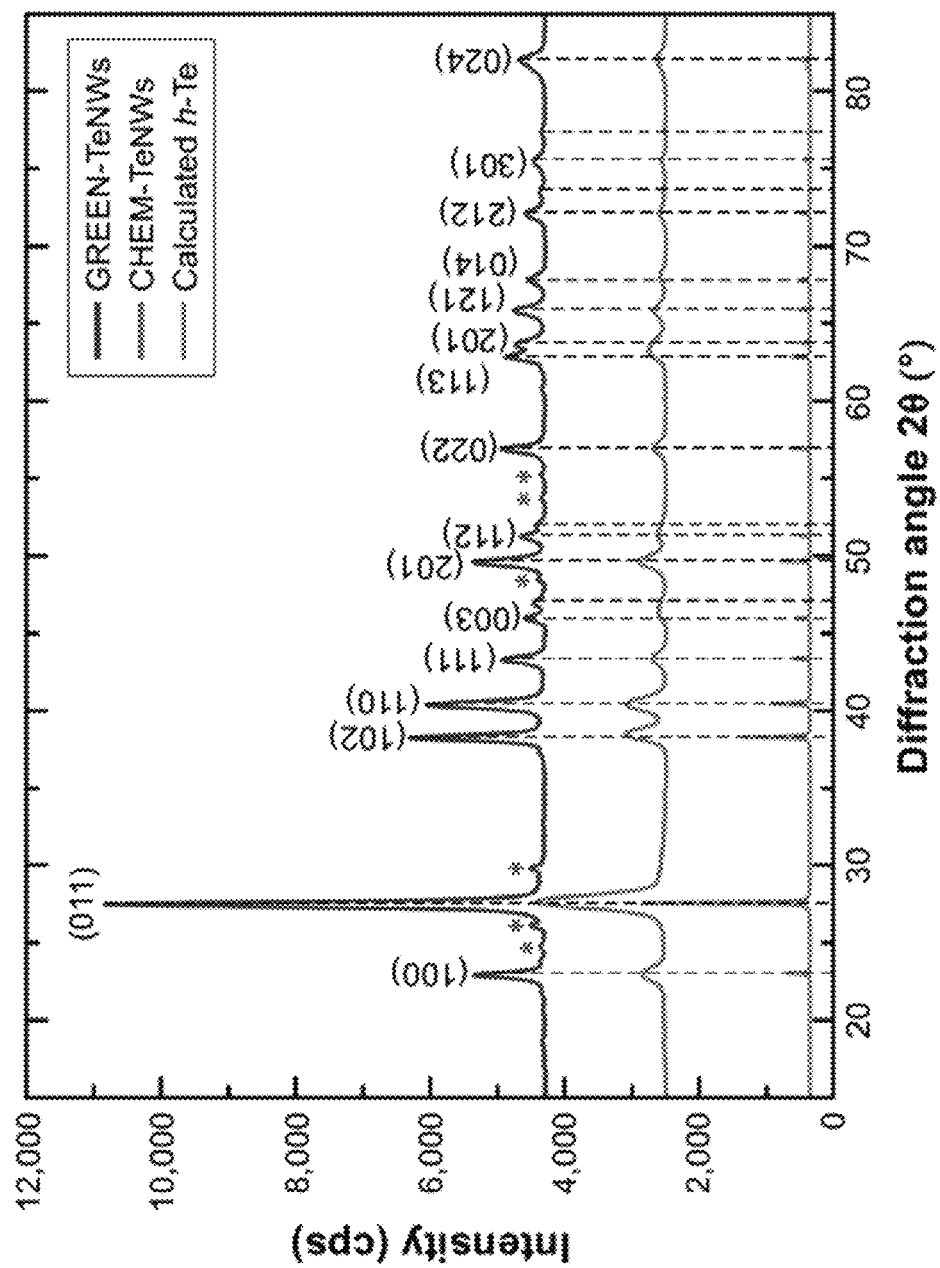
FIG. 13 shows a comparison between the experimental X-ray powder diffraction (XRD) patterns for GREEN-TeNWs (top spectrum) and CHEM-TeNWs (center spectrum) and the calculated XRD patterns (bottom spectrum) for bulk hexagonal Te (h-Te). The diffraction peaks marked with (*) may be related to Te-based oxides.

Tellurium has two allotropes, crystalline (hexagonal) and amorphous. It is known in the art that amorphous tellurium has a brown-black color and a powder morphology, and hexagonal crystalline tellurium has a silvery lustrous gray color with rigid crystals, and can have chains of Te atoms, that can form durable nanostructures of varying lengths. The XRD data herein supports hexagonal crystalline form. The XRD patterns for CHEM-TeNWs and GREEN-TeNWs are shown in FIG. 13 along with the calculated XRD pattern for the hexagonal Te structure (h-Te). Practically all the diffraction peaks in both experimental XRD patterns can be indexed to hexagonal Te structure (h-Te). Thus, the Te core of the nanowires comprises h-Te. In the case of the XRD spectrum of GREEN-TeNWs the presence of foreign phases related to Te-based oxides compounds is also detected and the diffraction peaks marked with "*" in FIG. 13 can be related to Te-based oxides. Amorphous Te is not detected in the XRD, but generally the limit of detection for amorphous forms in XRD can be challenging because amorphous materials form an amorphous "hump" in the XRD spectrum. The GREEN-TeNWs can consist essentially of h-Te because amorphous Te would form nanoparticles and not nanowires extending for microns with a width of 25±8 nm (or about 15 to about 35 nm). In this regard, to consist essentially of h-Te means that nanowire morphology is formed instead of amorphous brown-black nanoparticles (or aggregates of amorphous nanoparticles). The GREEN-TeNWs have a Te core that consists essentially of h-Te without impurities, crystalline or otherwise, that disrupt the integration with the outer coating, that disrupt the morphology or length of the wires, that disrupt the anticancer and cytocompatibility properties, and that disrupt the crystalline lustrous quality and durability. Based on morphological observations, the GREEN-TeNWs have a Te core that can consist of Te in the h-Te crystal form, and the Te core can have a coating that comprises starch. Table 2 (below) presents more detailed analyses.

For CHEM-TeNWs, three different phases are identified in Table 1 below, corresponding to elemental Te, sodium tellurate hydrate, and an organic compound. This last one is present on a relatively little amount compared with the other ones; it has been hypothesized that its presence comes from a hydrocarbon-based deposition of organic matter on the top of the sample either after the purification or after the preparation of the sample.

TABLE 1

List of identified patterns on XRD analysis of CHEM-TeNWs

| Reference Code | Score | Compound Name | Displacement (°2θ) | Scale Factor | Chemical Formula |
|---|---|---|---|---|---|
| 00-036-1452 | 64 | Tellurium, syn | 0.000 | 0.890 | Te |
| 00-032-1167 | 43 | Sodium Tellurate Hydrate | 0.000 | 0.170 | $Na_2Te_4O_9$ 14.5 $H_2O$ |
| 00-054-1863 | 17 | 5,7-Dihydroxy-4H-4-chromenone | 0.000 | 0.281 | $C_9H_6O_4$ |

XRD analysis of GREEN-TeNWs presents elemental Te, Te oxide, and organic compound phases (Table 2). The presence of Te oxide is related to the use of starch as a reducing agent as oxygen is integrated into the structure. Additionally, the organic compound is associated with the use of starch.

TABLE 2

List of identified patterns on XRD analysis of GREEN-TeNWs

| Reference Code | Score | Compound Name | Displacement (°2θ) | Scale Factor | Chemical Formula |
|---|---|---|---|---|---|
| 04-016-5121 | 44 | Tellurium | 0.000 | 0.840 | Te |
| 04-003-5854 | 36 | Tellurium oxide | 0.000 | 0.031 | $TeO_2$ |
| 00-043-1048 | 25 | Tellurium oxide | 0.000 | 0.028 | $TeO_3$ |

TABLE 2-continued

List of identified patterns on XRD analysis of GREEN-TeNWs

| Reference Code | Score | Compound Name | Displacement (°2θ) | Scale Factor | Chemical Formula |
|---|---|---|---|---|---|
| 00-067-1538 | 30 | Poly(ethylene glycol) 7500 | 0.000 | 0.093 | $((CH_2)_2O)n$ |

Figure 14:
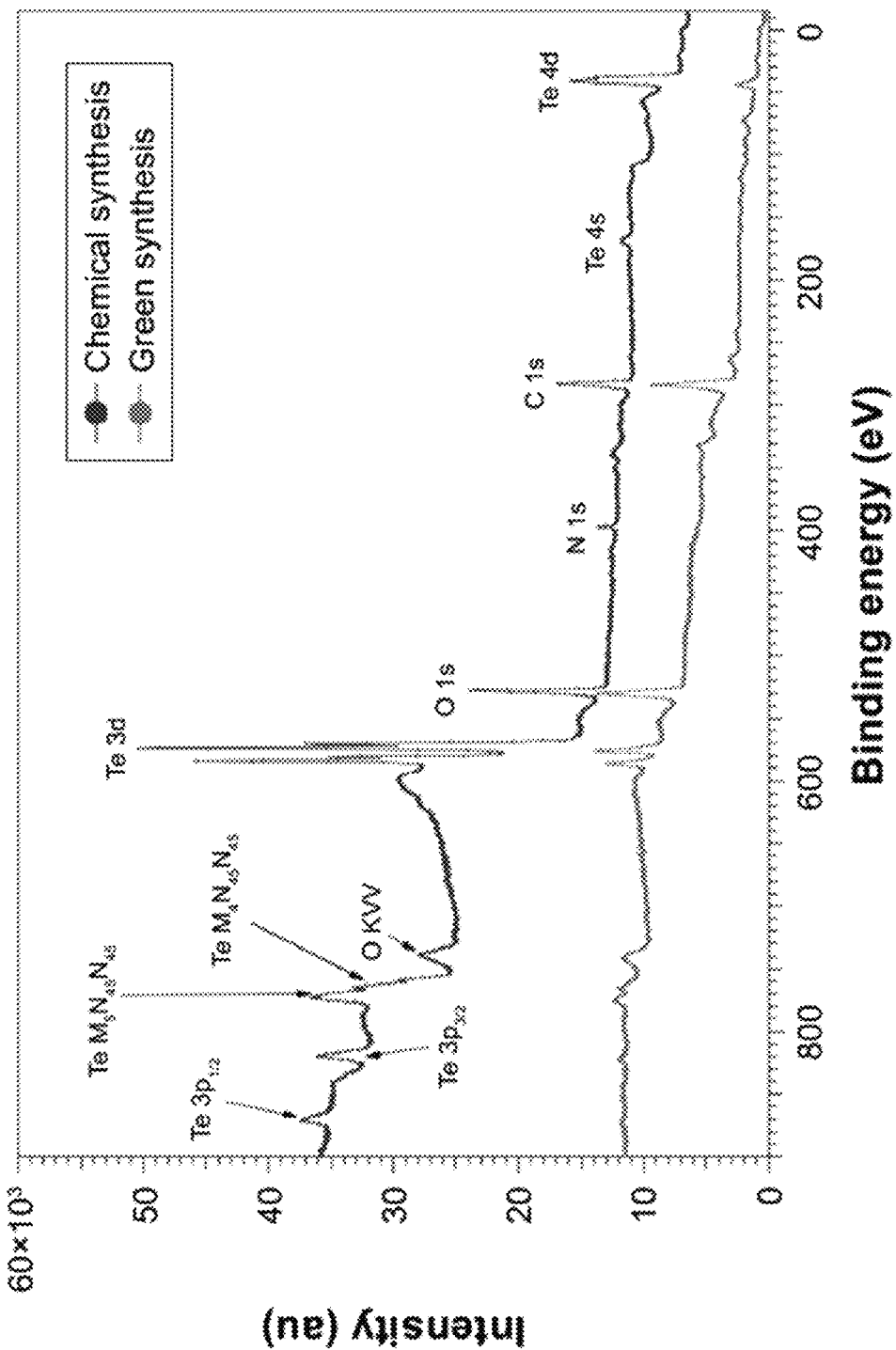
FIG. 14 shows X-ray photoelectron spectroscopy (XPS) spectra of CHEM-TeNWs (top spectrum) and GREEN-TeNWs (bottom spectrum); the wide scans have been normalized arbitrarily to the C 1s core level peak for comparison. Main features have been identified in the spectra.

X-ray photoelectron spectroscopy (XPS) for CHEM-TeNWs and GREEN-TeNWs is shown in FIG. 14. In FIG. 14, the wide scans are normalized arbitrarily to the C 1s core level peak for peak comparison, and the main features are identified in the spectra. Clear differences can be observed between the CHEM-TeNWs and GREEN-TeNWs. As the spectra are normalized to the C 1s core level peak, the higher intensity at the Te 3d core level for CHEM-TeNWs indicates that this compound has a higher content of Te than that in GREEN-TeNWs. In addition, the double structure for the Te 3d core level peaks (CHEM-TeNWs) is likely to indicate that this element is partially oxidized. It clearly appears that GREEN-TeNWs have no nitrogen (absence of N 1s core level peak) as compared to the CHEM-TeNWs; these differences can be due to the use of hydrazine and $NH_3$ as reducing agents in the chemical synthetic approach.

Figure 15:
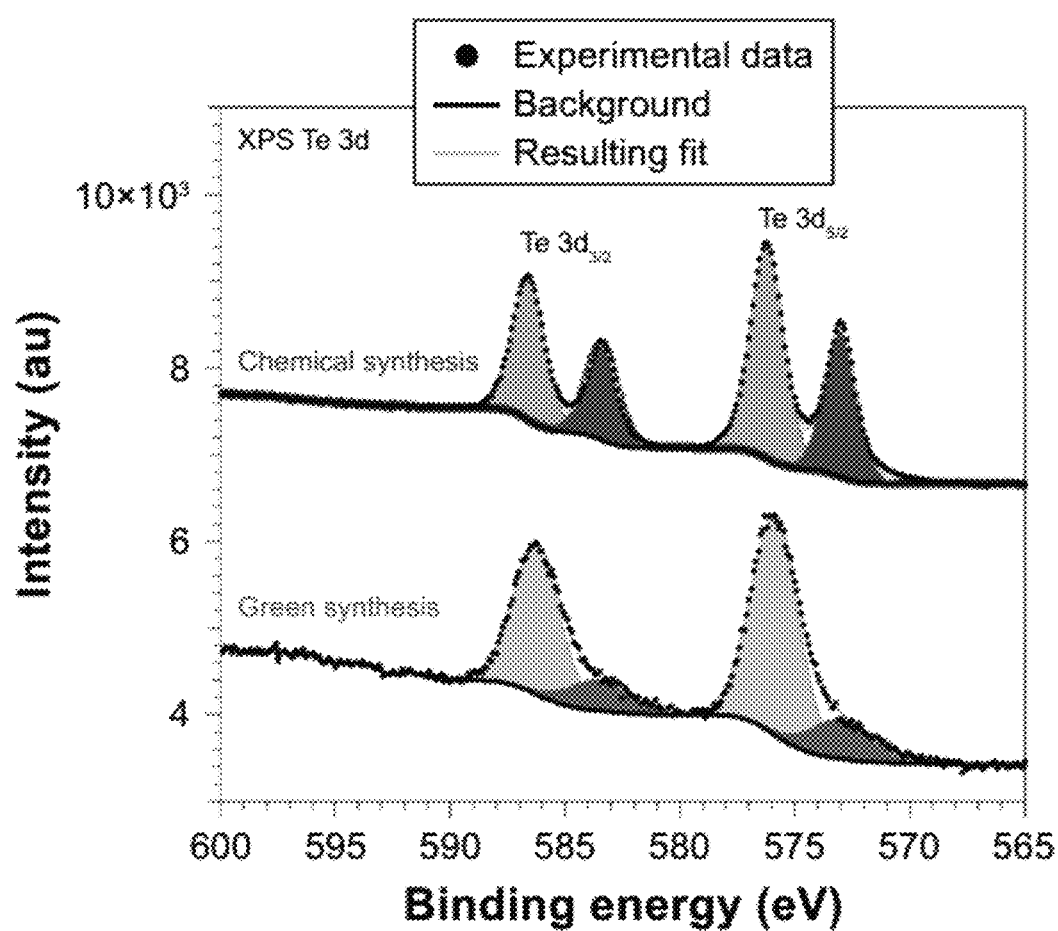
FIG. 15 shows XPS spectra recorded at the Te 3d core levels for samples synthesized through the chemical (top trace) and green (bottom trace) routes.

Differences between the CHEM-TeNWs and GREEN-TeNWs are better appreciated when comparing the Te 3d core levels as shown in FIG. 15. The spectra are normalized to the Te $3d_{5/2}$ oxide component (at a binding energy of 576 eV) and shifted (overlaid) vertically for comparison. As can be observed, metallic and oxide components can clearly be identified. The metallic components are located at 573 eV (chosen as a reference in order to correct the charging effects) and 583.4 eV for the Te $3d_{5/2}$ and Te $3d_{3/2}$ peaks, respectively, whereas the oxide components are located at 576 eV and 586.6 eV for the Te $3d_{5/2}$ and Te $3d_{3/2}$ structures, respectively. It also clearly appears that GREEN-TeNWs have more of a Te oxide (79%) component than the CHEM-TeNWs (61% oxide) as seen previously in the XRD results.

Figure 16:
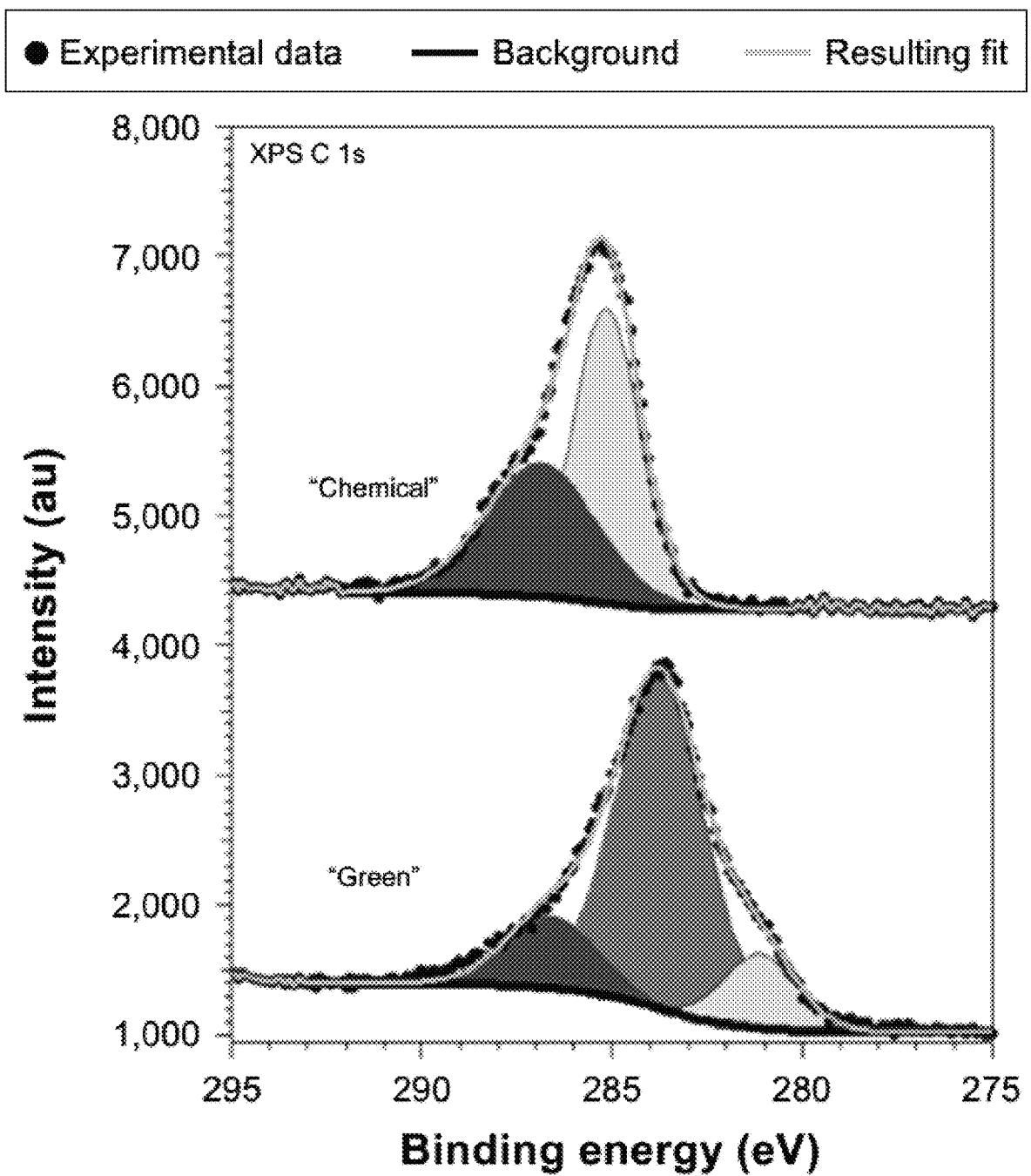
FIG. 16 shows XPS spectra recorded at the C 1s core levels for samples synthesized through the chemical (top trace) and green (bottom trace) routes.
Figure 17:
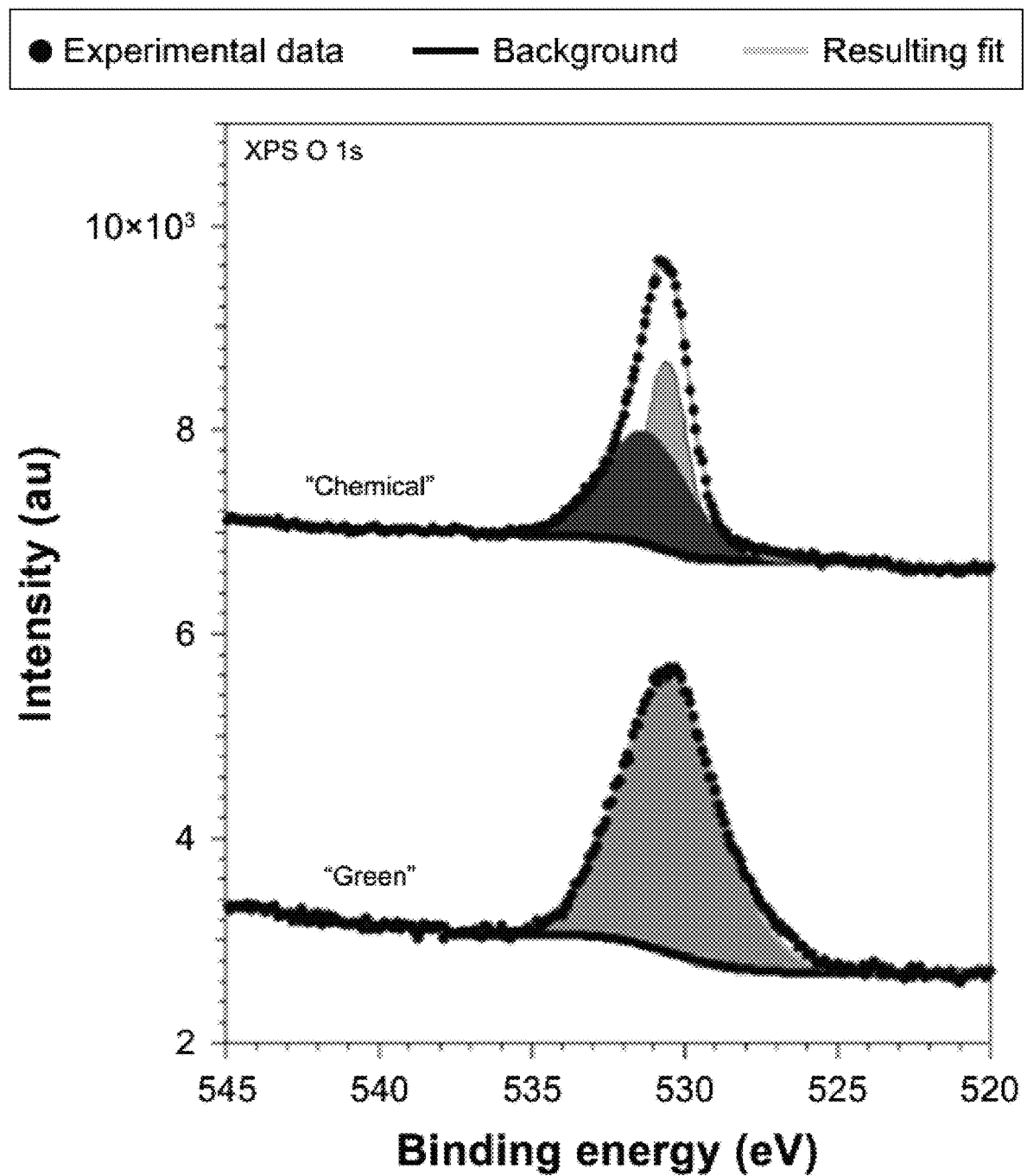
FIG. 17 shows XPS spectra recorded at the O 1s core levels for samples synthesized through the chemical (top trace) and green (bottom trace) routes.

The CHEM-TeNWs and GREEN-TeNWs also present differences at the C 1s and O 1s core levels (FIGS. 16-17). The C 1s core levels spectra (FIG. 16) can be fitted with the following minimum number of components at 281.1 eV (13%), 283.7 eV (71%), and 286.6 eV (16%) for GREEN-TeNWs and 285.1 eV (57%) and 286.8 eV (43%) for CHEM-TeNWs. The peaks located at 286.6 eV and 286.8 eV can be ascribed to hydroxyl (C—O/C—OH) groups, meaning that CHEM-TeNWs have more hydroxyl groups than GREEN-TeNWs. At a lower binding energy, a peak located at 285.1 eV can be identified in CHEM-TeNWs (see top of FIG. 16). This peak corresponds to the presence of either C—C or C—H bonds in the sp3 tetrahedral configuration, and surprisingly, it was not observed in GREEN-TeNWs. Instead, two peaks at lower binding energies of 281.1 eV and 283.7 eV were identified on the spectrum of the GREEN-TeNWs (see bottom of FIG. 16). The peak at 283.7 eV could be ascribed to C—C bonds in the sp2 configuration, while the less abundant component with an XPS peak at 281.1 eV could not be clearly identified. It is inferred that this last component corresponds to C atoms weakly bonded. Thus, no evidence of the presence of carbonyl (C═O at 288.1 eV) or carboxyl (O—C═O at 289.0 eV) groups could be observed.

In the case of the O 1s core level spectra (FIG. 17), the spectrum corresponding to GREEN-TeNWs could be fitted with a single component at 530 eV, while CHEM-TeNWs have two components located at 530.6 eV (44%) and 531.3 eV (56%). These relatively weak binding energies suggest that the oxygen atoms are weakly bonded and do not correspond to O—C bonds that would appear at a binding energy of around 533 eV. This in turn agrees with the absence of carbonyl and carboxyl groups in the C 1s spectra.

Keeping in mind that X-ray photoelectron spectroscopy (XPS) is a surface-sensitive quantitative spectroscopic technique, chemical analysis performed at the Te 3d, O 1s, N 1s, and C 1s core level peaks reveals the composition shown below in Table 3, providing further insight into the coating of the GREEN-TeNWs. XPS analysis can penetrate about 5-20 Å, allowing for surface specific, rather than bulk chemical analysis, compared to the ATR (FT-IR) data shown in FIG. 12.

TABLE 3

XPS Chemical composition (in percentage atomic concentration) extracted from the Te 3d, O 1s, N 1s, and C 1s core level peaks

| Element | GREEN-TeNWs | CHEM-TeNWs |
|---|---|---|
| Tellurium | 2.6 | 17.1 |
| Oxygen | 67.8 | 31.5 |
| Nitrogen | — | 5.3 |
| Carbon | 29.6 | 46.1 |

To determine the effect of the coating present on GREEN-TeNWs on the proliferation of cells, in vitro cytotoxicity assays were performed with HDF cells and melanoma cells (ATCC® CRL-1619™). Data from the nanowire treatments were compared with a control that contained only cells and media. A comparison was made between human dermal fibroblast (HDF) and melanoma cells with the aim of determining potential anticancer activity (and potential toxicity toward normal cells). The same experiments were performed using chemical and green-synthesized nanowires.

Figure 18:
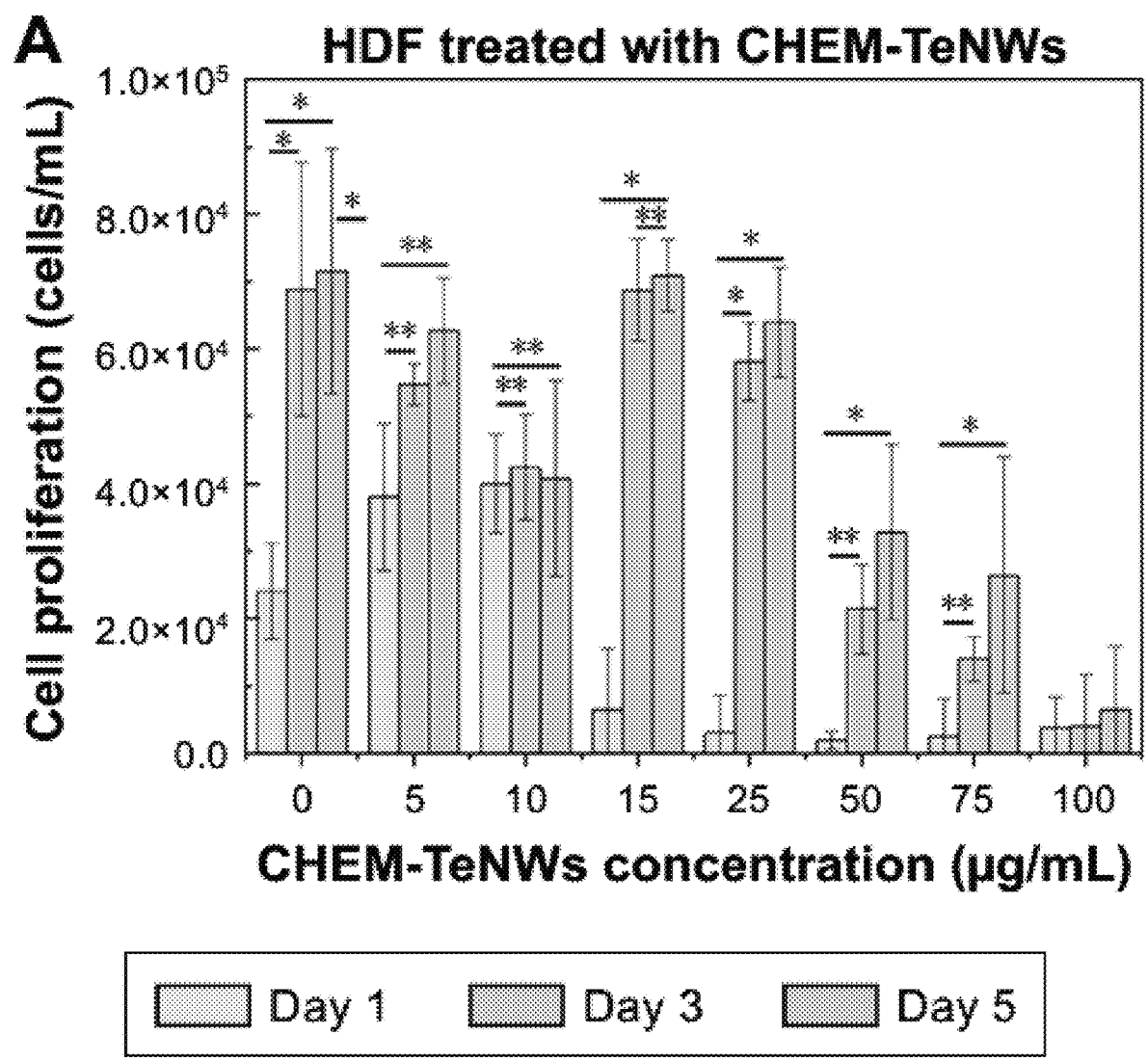
FIG. 18 shows MTS assays on human dermal fibroblasts (HDF) treated with CHEM-TeNWs at concentrations of 0, 5, 10, 15, 25, 50, 75, and 100 micrograms/mL. For each concentration, the plotted day 1 data is the leftmost bar, the day 3 data is the center bar, and the day 5 data is the rightmost bar. N=3; data are presented as mean±sD; *$P<0.01$, **$P<0.005$.
Figure 19:
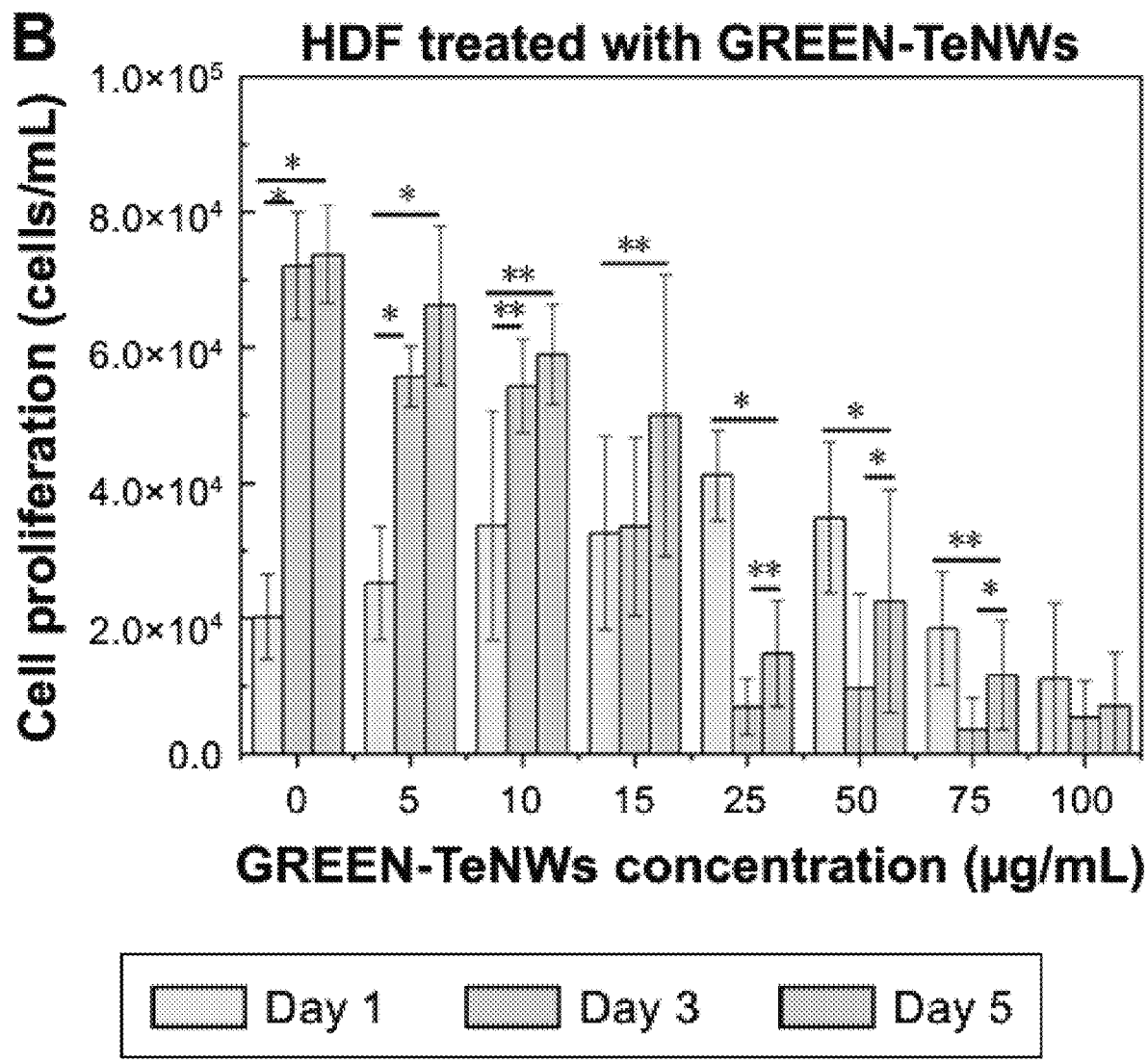
FIG. 19 shows MTS assays on human dermal fibroblasts (HDF) treated with GREEN-TeNWs at concentrations of 0, 5, 10, 15, 25, 50, 75, and 100 micrograms/mL. For each concentration, the plotted day 1 data is the leftmost bar, the day 3 data is the center bar, and the day 5 data is the rightmost bar. N=3; data are presented as mean±sD; *$P<0.01$, **$P<0.005$.

For HDF experiments, nanowires at a concentration between 5 and 100 µg/mL were tested. For CHEM-TeNWs, the same proliferation trend was observed within the third and fifth day for concentrations up to 15 µg/mL compared with the control, which is 0 µg/mL (FIG. 18). However, the number of cells was less than that for the control in all the cases. Larger concentrations showed degeneration of the cell proliferation. When GREEN-TeNWs were tested on the cells, a similar proliferation trend was observed for each of the concentrations (FIG. 19). An especially unusual behavior was shown at levels between 15 and 75 µg/mL, with a higher number of cells growing within the third and the fifth day compared with the first 24 hours. When both nanostructures were compared (e.g., FIG. 22), it can be concluded that the green-synthesized structures enhanced cell proliferation over a broader range of concentrations compared with the chemical synthetic ones.

The cytotoxic effect of Te nanostructures is the result of active physicochemical interactions of elemental Te with the functional groups of intracellular proteins and the bases and phosphate groups in DNA. While cytotoxicity was apparent for the CHEM-TeNWs (FIG. 18), it is believed that the enhanced biocompatibility in GREEN-TeNWs (FIG. 19) is due to the presence of a natural, organic coating that encompasses the Te core. The presence of a carbon layer as the natural coating introduces a biodegradable material that can reduce toxicity. Any biodegradable and biocompatible coating surrounding the Te core of the GREEN-TeNWs can provide GREEN-TeNWs with enhanced biocompatibility, cytological compatibility, and with anticancer activity. A coating comprising one or more polymers, including cross-linked or chemically modified naturally occurring biopolymers such as polysaccharide, starch, glycogen, gelatin, protein, or a synthetic but biodegradable and non-toxic coating, can enhance biocompatibility and cytological compatibility with normal cells and tissues without degrading anticancer activity. Such engineered coatings also can be utilized to target the GREEN-TeNWs to specific areas or tumors.

Figure 20:
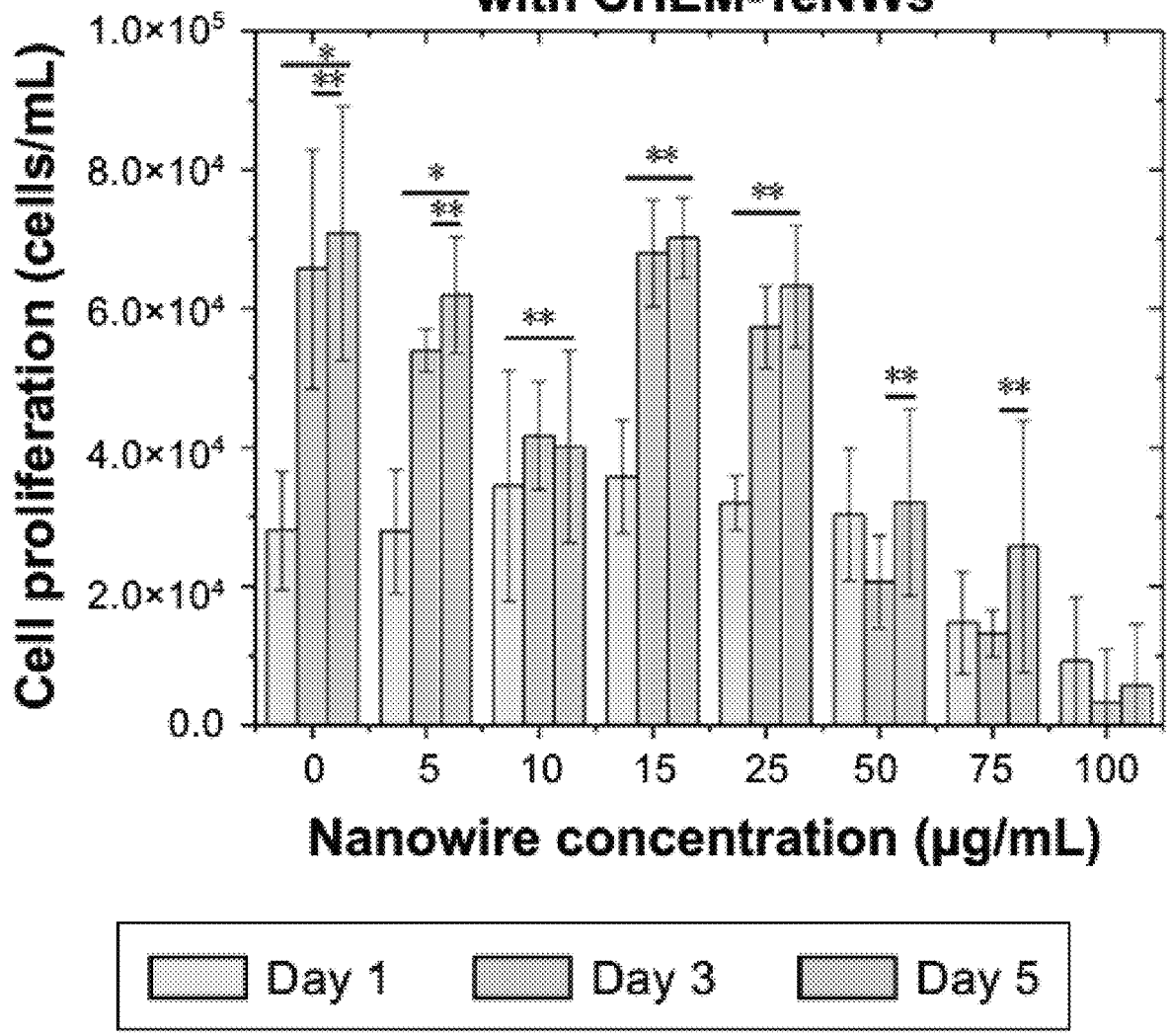
FIG. 20 shows MTS assays on melanoma cells (ATCC® CRL-1619™) treated with CHEM-TeNWs at concentrations of 0, 5, 10, 15, 25, 50, 75, and 100 micrograms/mL. For each concentration, the plotted day 1 data is the leftmost bar, the day 3 data is the center bar, and the day 5 data is the rightmost bar. N=3; data are presented as mean±sD; *$P<0.01$, **$P<0.005$.
Figure 21:
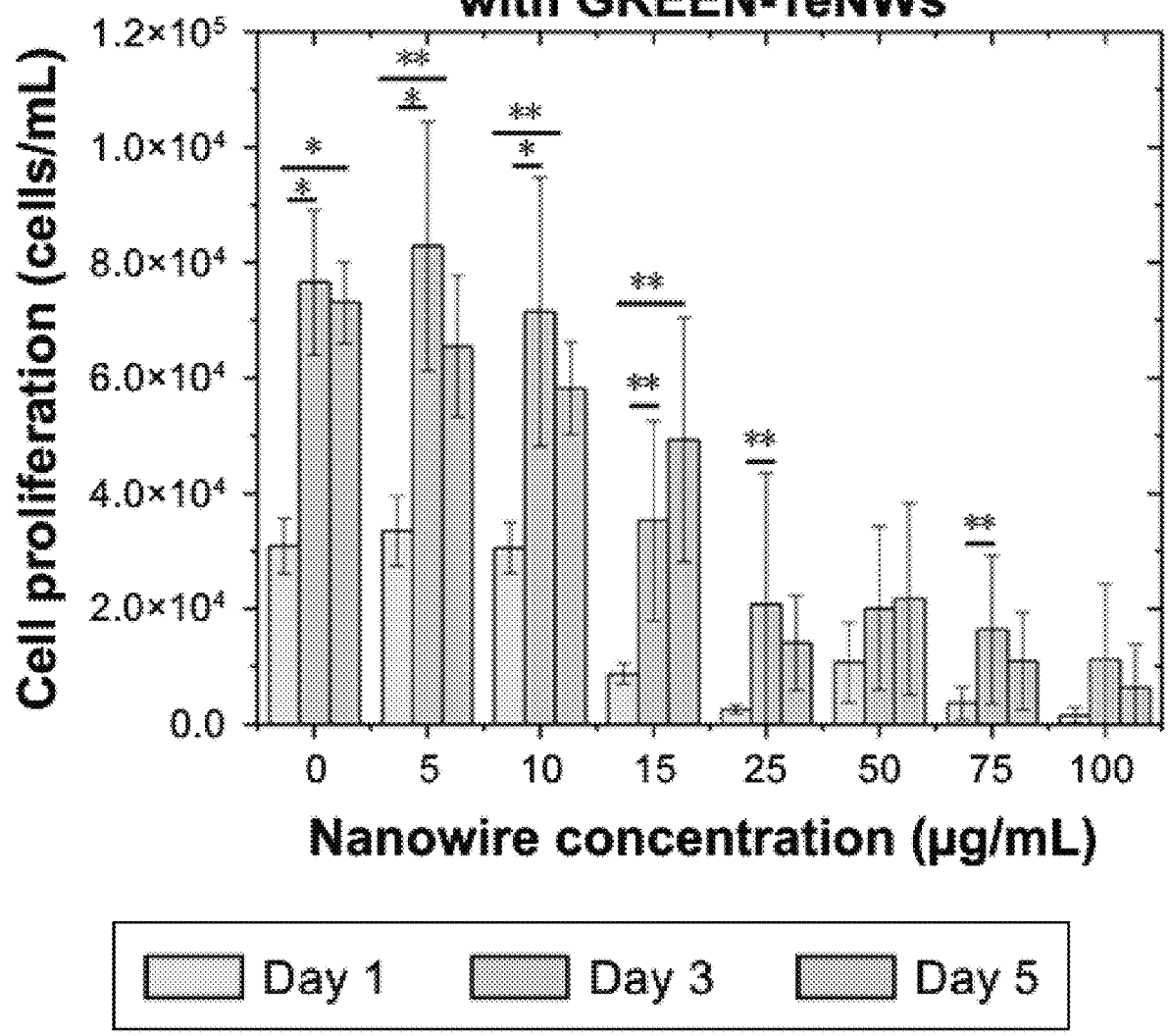
FIG. 21 shows MTS assays on melanoma cells (ATCC® CRL-1619™) treated with GREEN-TeNWs at concentrations of 0, 5, 10, 15, 25, 50, 75, and 100 micrograms/mL. For each concentration, the plotted day 1 data is the leftmost bar, the day 3 data is the center bar, and the day 5 data is the rightmost bar. N=3; data are presented as mean±sD; *$P<0.01$, **$P<0.005$.

When melanoma cells were treated with CHEM-TeNWs, cell proliferation showed a similar trend as that of the control at concentrations up to 25 µg/mL (FIG. 20). GREEN-TeNWs showed a similar behavior (FIG. 21). Nonetheless, levels between 10 and 100 µg/mL showed a delay in the cell proliferation compared with the control over the tested time period. It has been hypothesized that TeNWs have the potential ability to slow down the signaling processes present in cancerous cells due to the effect of Te. Therefore, it is proposed that both synthesis methods produce nanostructures with anticancer properties, but specifically this behavior was particularly enhanced in the case of the green synthetic structures (see FIG. 23). Thus, not only were the GREEN-TeNWs produced with significantly fewer toxic materials, but their properties toward enhancing healthy cell proliferation and decreasing cancer cell proliferation were also greater.

Figure 22:
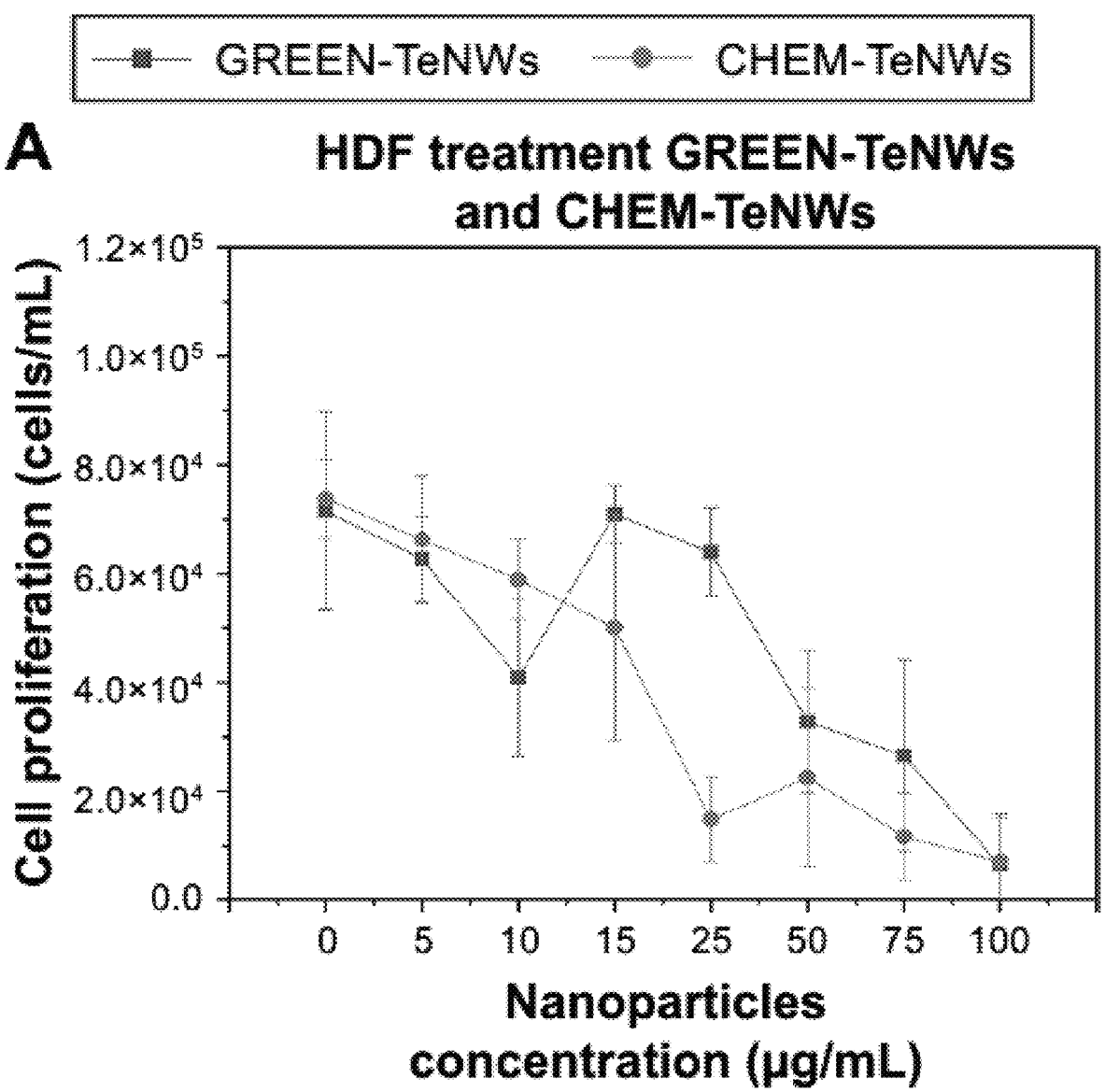
FIG. 22 shows a comparison between MTS assays for CHEM-TeNWs (●) and GREEN-TeNWs (■) for HDF cells at the fifth day of experiment.
Figure 23:
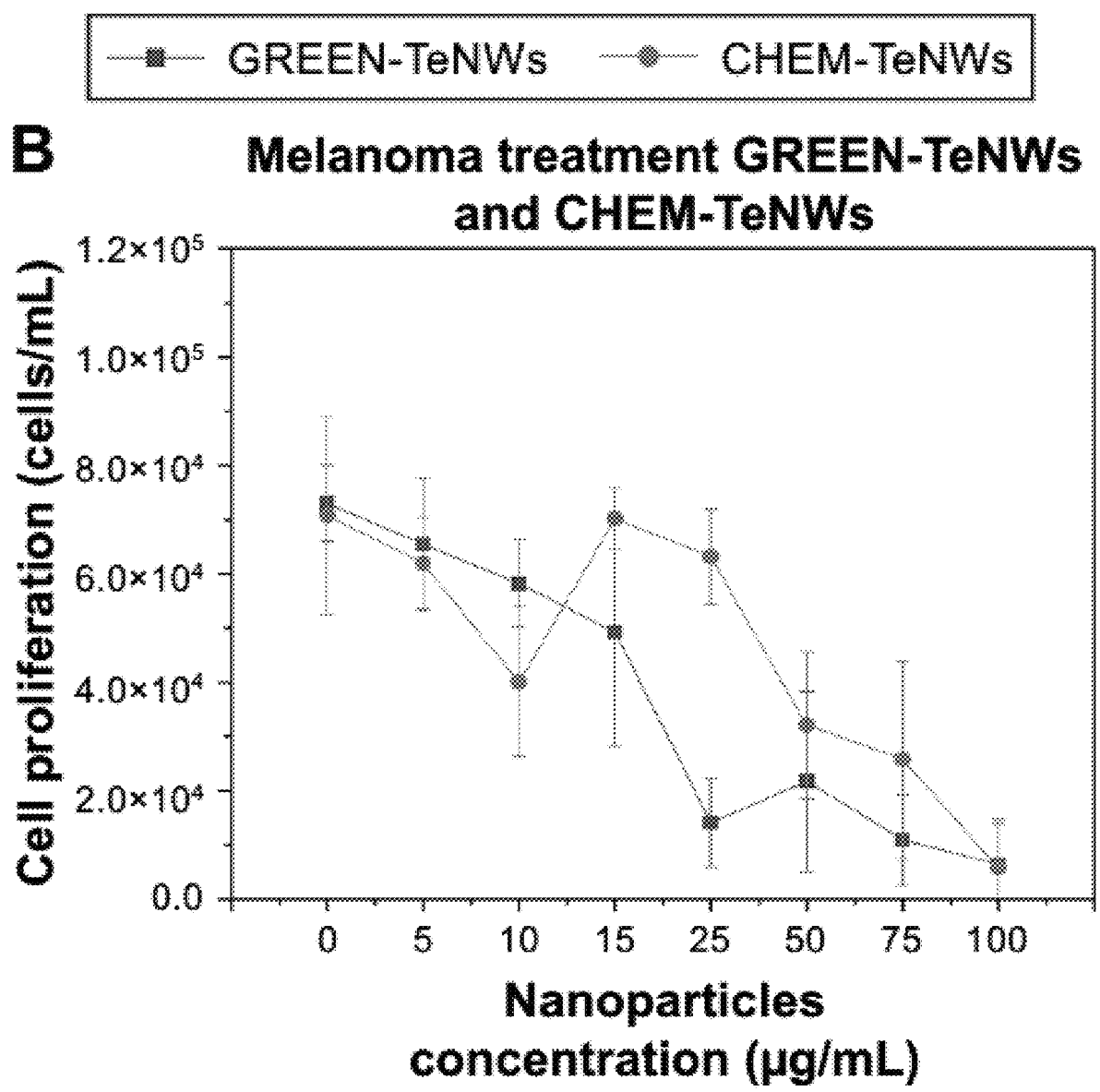
FIG. 23 shows a comparison between MTS assays for CHEM-TeNWs (●) and GREEN-TeNWs (■) for melanoma cells at the fifth day of experiment.

To describe FIGS. 22-23 in more detail, a comparison was done on the fifth day of the experiments between samples to show the tendency of both cell compatibilities with HDF cells (FIG. 22) and cytotoxic effects with melanoma cells (FIG. 23). The low cytotoxicity for HDF cells can be appreciated especially at high concentrations of TeNWs, with a noticeable difference between CHEM-TeNWs, with higher cytotoxicity for HDF cells, and GREEN-TeNWs, which allow for a high cell proliferation. At low concentrations, between 5 and 15 µg/mL, the difference in terms of biocompatibility was almost inappreciable. The biggest difference was observed at a concentration of 25 µg/mL. For experiments with cancerous cells, the opposite occurred. GREEN-TeNWs did not allow for the proliferation of melanoma cells at concentrations ranging between 15 and 100 µg/mL. As with HDF cells, the bigger difference was observed for a concentration of 25 µg/mL. Therefore, it is possible to hypothesize that at a concentration of 25 µg/mL of GREEN-TeNWs, both the maximum biocompatibility for HDF and the maximum cytotoxic effect for melanoma cells can be achieved in comparison with the same concentration of CHEM-TeNWs. As a general view, the behavior of GREEN-TeNWs after 5 days in terms of low and high cytotoxicity for HDF and melanoma cells, was enhanced in comparison with CHEM-TeNWs. Based on FIGS. 22-23, the green chemistry synthesized Te nanowires (GREEN-TeNWs) outperformed those produced by traditional synthetic chemical methods. For example, the GREEN-TeNWs inhibited cancerous cell growth at least twice more than non-cancerous cell growth from 15-35 µg/mL, or about 25 µg/mL.

$IC_{50}$ values were calculated for all the experiments in Table 6, with the aim of showing the minimum inhibitory concentration for both HDF and melanoma cells. This value was obtained after 5 days of experiments, measuring the potency of the nanowires to inhibit the normal biological functioning of the cells (see Example 3).

The interaction between the cells and the nanostructures was studied using SEM imaging of melanoma and HDF cells. Different concentrations, 100, 50, and 0 µg/mL, of TeNWs were tested in order to elucidate the mechanism of cell death on both cell types. SEM imaging allowed the observation of modifications in the membrane and the shape of cells.

Figure 24:
FIG. 24 shows a scanning electron microscope (SEM) image of interaction between human dermal fibroblast (HDF) cells and GREEN-TeNWs at 50 μg/mL.
Figure 25:
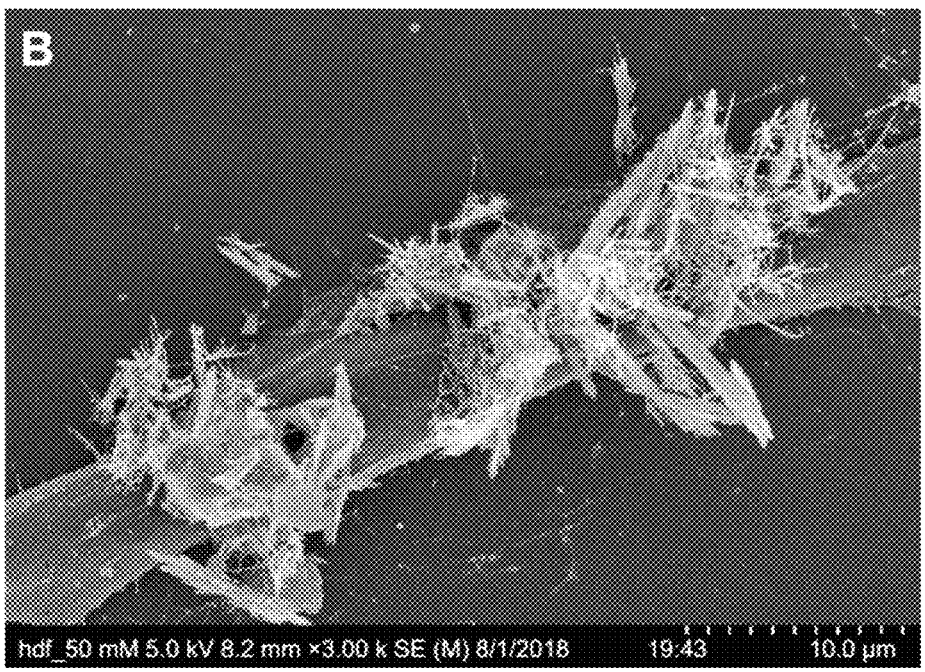
FIG. 25 shows a scanning electron microscope (SEM) image of interaction between human dermal fibroblast (HDF) cells and GREEN-TeNWs at 50 μg/mL.
Figure 26:
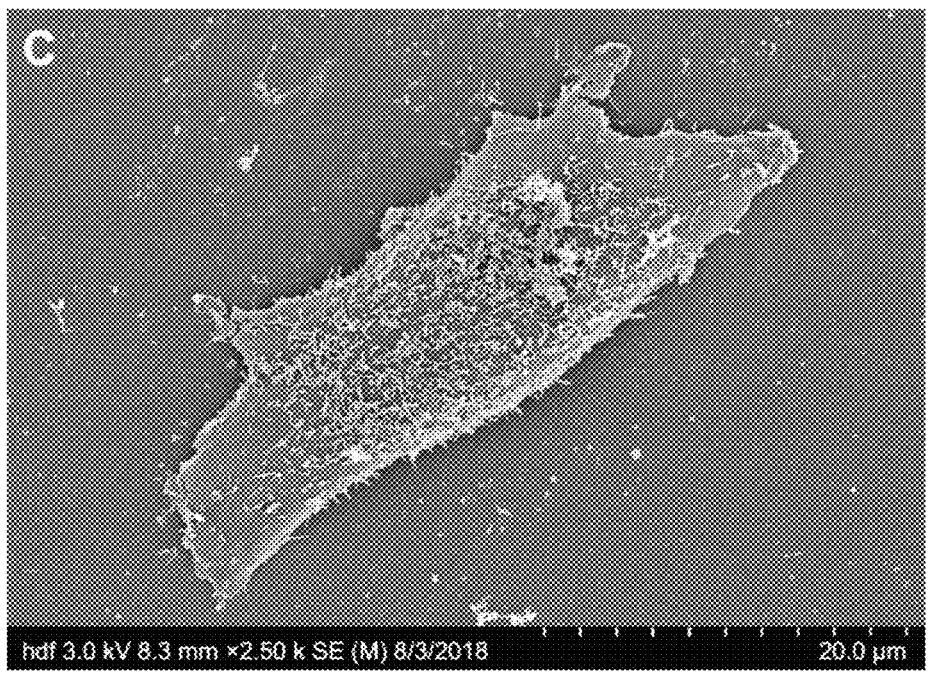
FIG. 26 shows a control scanning electron microscope (SEM) image of human dermal fibroblast (HDF) cells without GREEN-TeNWs (0 μg/mL).

For HDF cells, NWs were found to be in contact with the cells; however, no interaction between them was observed at lower concentrations. FIGS. 24-25 are both 50 µg/mL GREEN-TeNWs with HDF cells. At 50 µg/mL, GREEN-TeNWs surrounded the HDF cells without producing any cell damage when compared to the control, which is 0 µg/mL (FIG. 26). In FIGS. 24-25, the membrane remained intact without any sign of swelling or blebbing. Thus, it has been hypothesized that the presence of starch encases the TeNWs and prevents their interaction with HDF cells.

Figure 27:
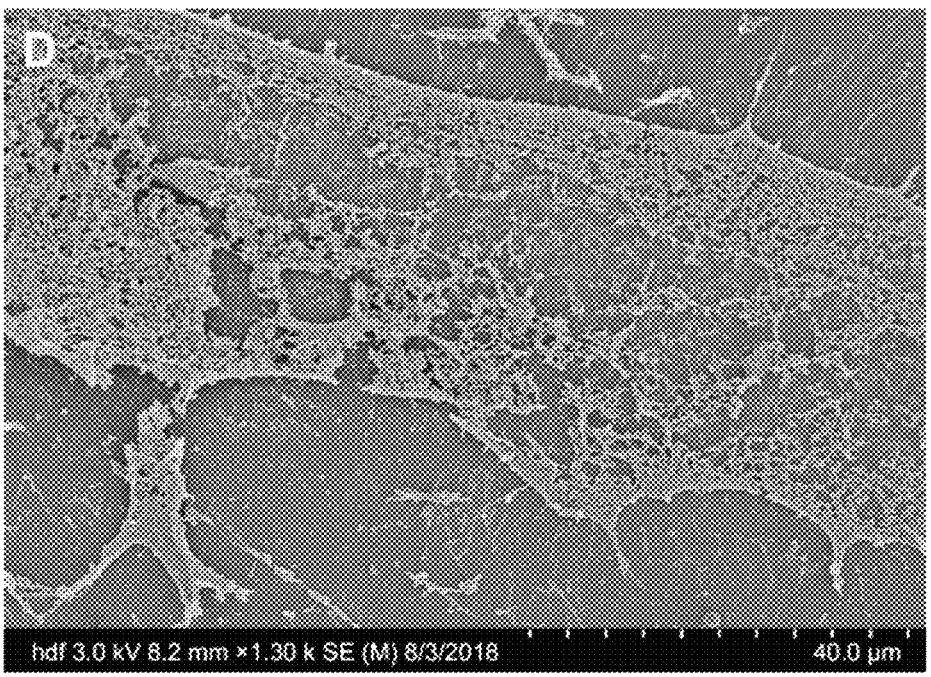
FIG. 27 shows a scanning electron microscope (SEM) image of interaction between human dermal fibroblast (HDF) cells and GREEN-TeNWs at 100 μg/mL.

Nevertheless, higher concentrations of 100 µg/mL GREEN-TeNWs seem to produce necrosis on cells as is shown in FIG. 27. Swelling of the cell due to a hydration process and discontinuities on the membrane previous to its rupture are indicated as signs of necrosis. SEM captured the different stages of the rupture of the cytoplasmic membrane due to a swelling process (FIG. 27); hence, the mechanism of death was interpreted as necrosis.

Figure 28:
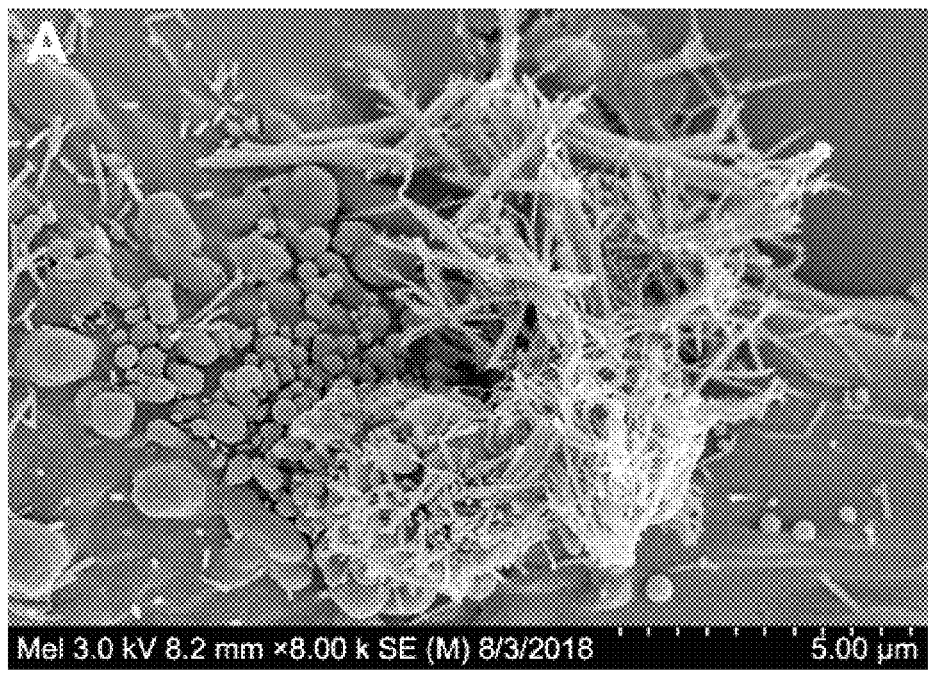
FIG. 28 shows a scanning electron microscope (SEM) image of melanoma cells with blebbing of the cell membrane observed during interaction between melanoma cells and GREEN-TeNWs.
Figure 29:
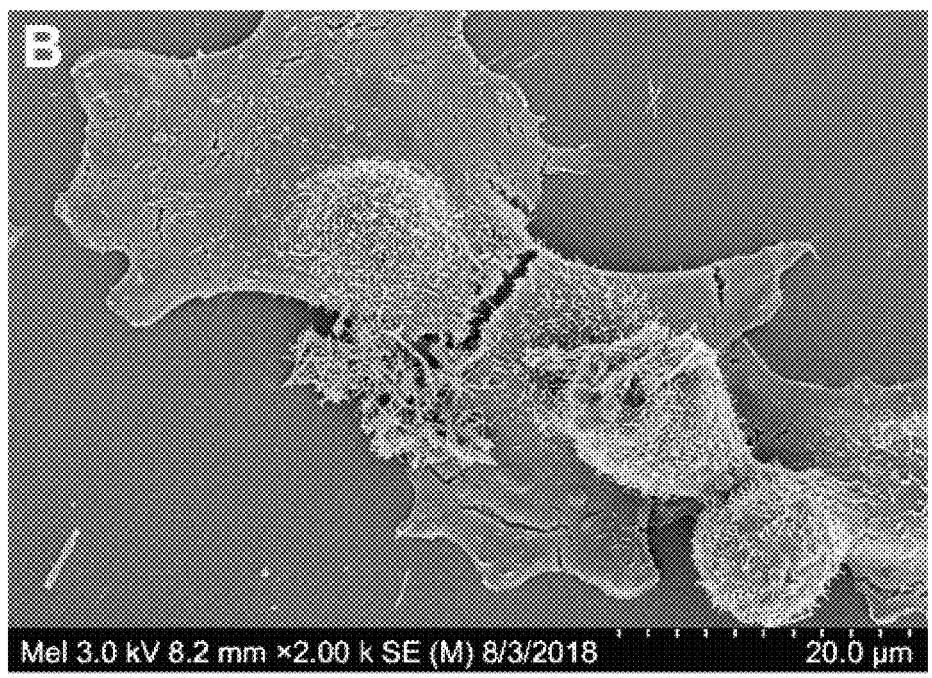
FIG. 29 shows a scanning electron microscope (SEM) image of melanoma cells with rupture of the cell membrane observed during interaction between melanoma cells and GREEN-TeNWs.
Figure 30:
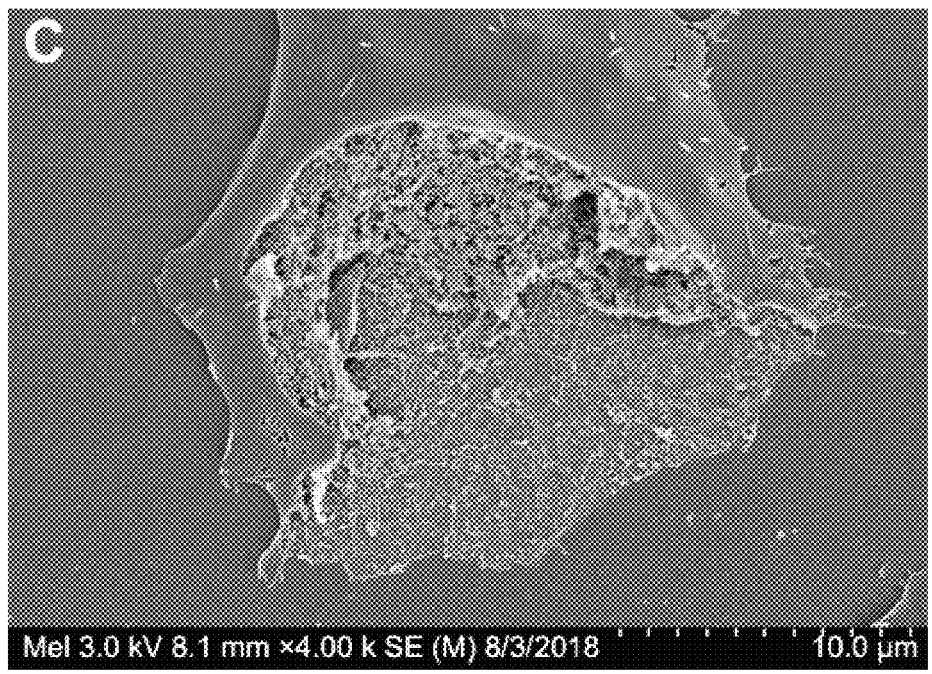
FIG. 30 shows a scanning electron microscope (SEM) image of melanoma cells with rupture of the cell membrane observed during interaction between melanoma cells and GREEN-TeNWs.
Figure 31:
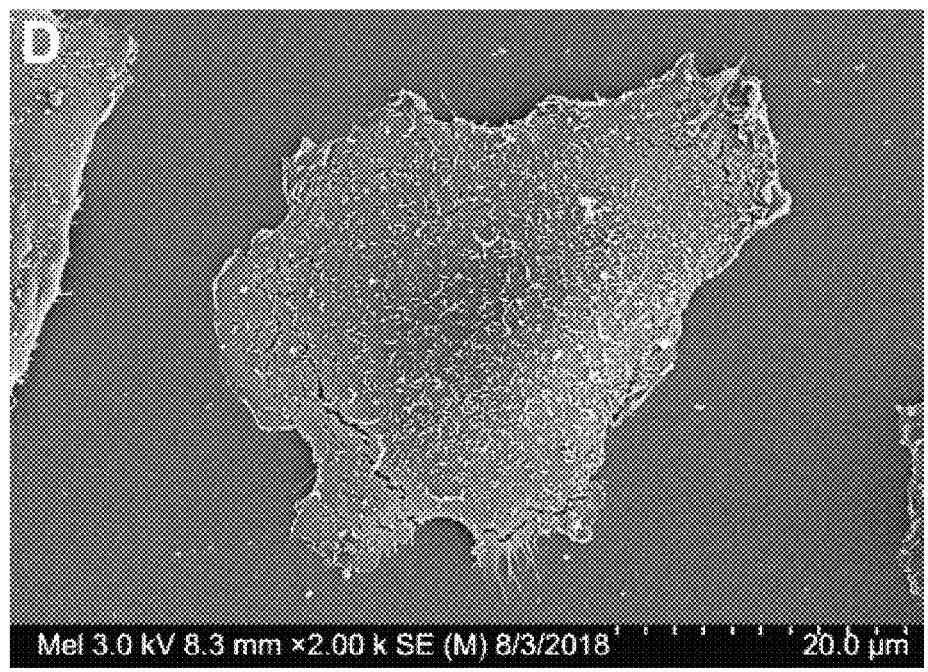
FIG. 31 shows a control scanning electron microscope (SEM) image of melanoma cells without GREEN-TeNWs (0 μg/mL).

In contrast, blebbing (FIG. 28) was observed on melanoma cells in comparison with the control (FIG. 31), indicating a process of apoptosis. These blebbing formations on the membrane are associated with a rearrangement in the cytoskeleton, which eventually ended in the rupture in fragments of the cell. It has been hypothesized that differently than HDF, GREEN-TeNWs interact with melanoma cells by inducing chemical signaling, which leads to apoptosis, hence reducing cell proliferation by breaking cells apart (FIGS. 29-30). It has been elucidated that different mechanisms of death are possible due to the use of different kinds of cells.

Figure 32:
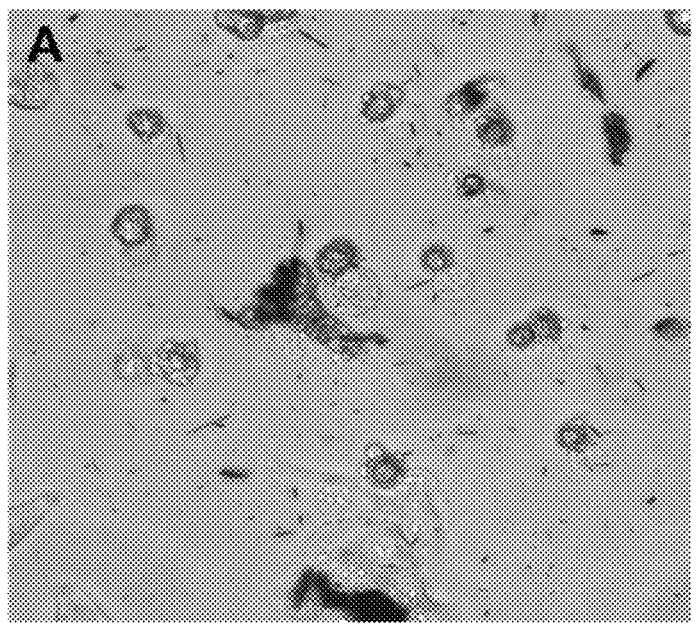
FIG. 32 shows an optical microscope image of human dermal fibroblast (HDF) cells cultured in the presence of CHEM-TeNWs for 24 hours.
Figure 33:
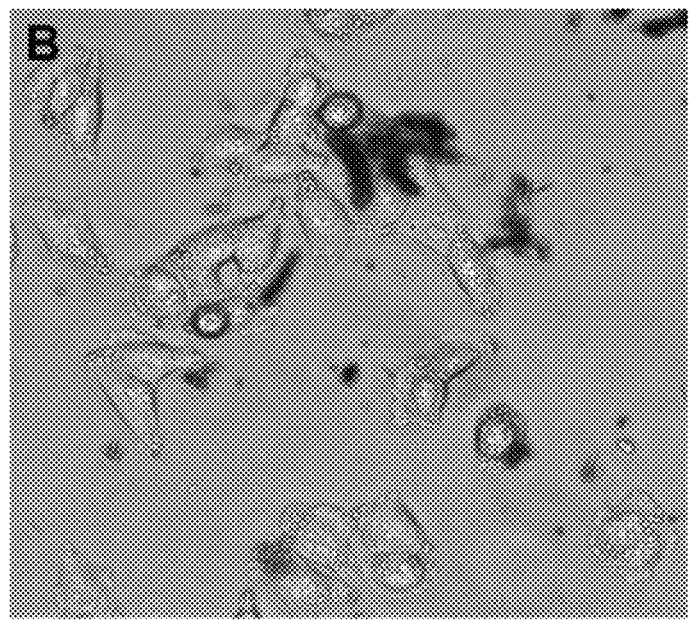
FIG. 33 shows an optical microscope image of human dermal fibroblast (HDF) cells cultured in the presence of GREEN-TeNWs for 24 hours.
Figure 34:
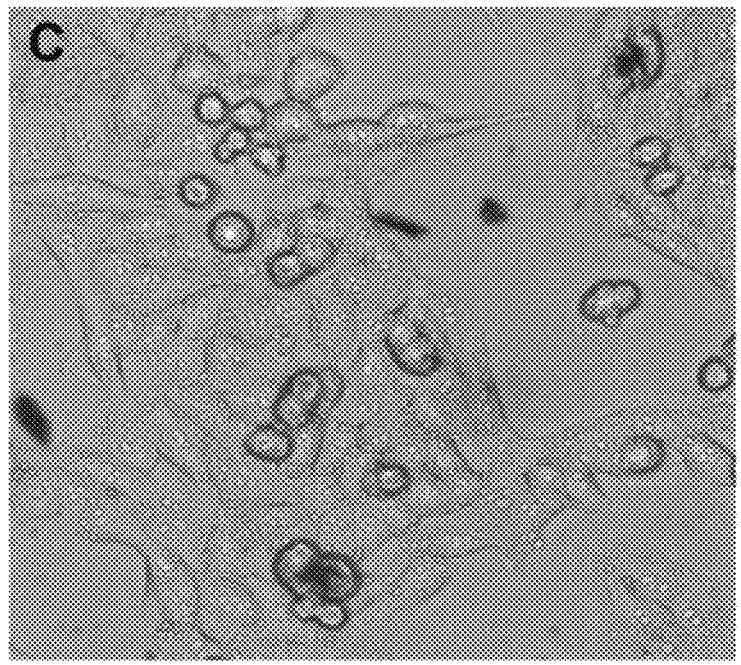
FIG. 34 shows an optical microscope image of human melanoma cells cultured in the presence of CHEM-TeNWs for 24 hours.
Figure 35:
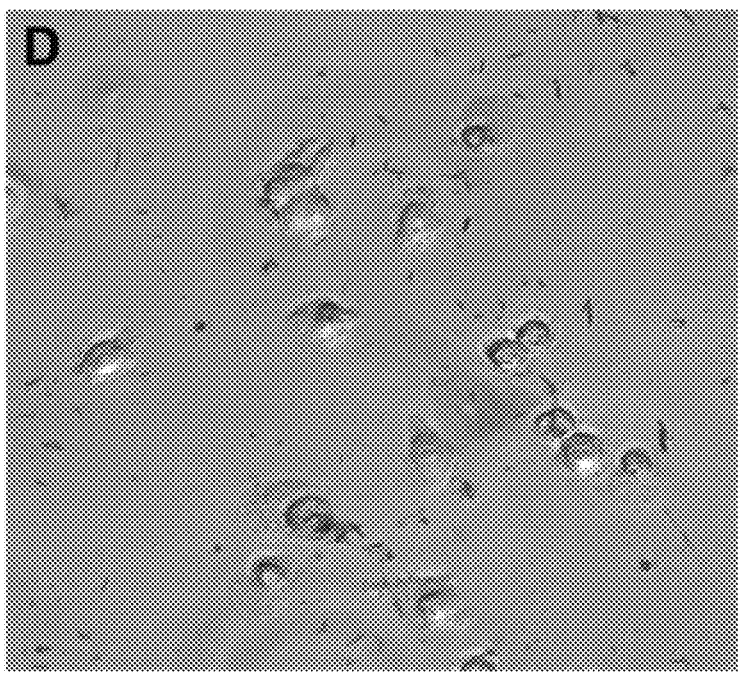
FIG. 35 shows an optical microscope image of human melanoma cells cultured in the presence of GREEN-TeNWs for 24 hours.

Optical microscopy showed preliminary results of how different cells behaved in the presence of both GREEN-TeNWs and CHEM-TeNWs. After 24 hours of treatment, 50 µg/mL CHEM-TeNWs (FIG. 32) showed a remarkable disturbance in the growth of HDF cells after 24 hours of treatment, with poor cell development, while the same concentration of GREEN-TeNWs (FIG. 33) allowed the development of the cells to a large extent. When melanoma human cells were tested with the same concentration of CHEM-TeNWs (FIG. 34), the cells showed better development than the ones cultured with GREEN-TeNWs (FIG. 35) for the same period.

To summarize, nanowires produced by two different synthetic approaches, (1) a traditional chemical method (CHEM-TeNWs), and (2) a green chemistry method (GREEN-TeNWs), were evaluated to elucidate differences in the cytocompatibility and anticancer behavior of the nanowires. Experiments with healthy fibroblasts and cancerous melanoma cells were carried out over a range of concentrations between 5 and 100 µg/mL using nanowires produced using both methods. Both, an improvement in cell proliferation of HDF cells and a decrease in the proliferation of cancerous cells was observed when GREEN-TeNWs were used compared to CHEM-TeNWs. An enhancement in the proliferation of healthy fibroblast proliferation was observed with GREEN-TeNWs compared to the CHEM-TeNWs. As such, GREEN-TeNWs have the potential for use in a wide range of medical applications and treatments. The green synthetic approach described herein offers important improvements in terms of safety, economical, efficiency, and biocompatibility for biomedical applications, overcoming the main drawbacks of traditional Te nanowire chemical approaches.

EXAMPLES

Example 1

Synthesis of Green Biogenic TeNWs and Chemical TeNWs

Tellurium Nanowire Synthesis and Purification

For a traditional chemical synthesis route, following a variation of the protocol described by Hong et al. [38], in a typical process of integration, sodium tellurite ($Na_2TeO_3$) (Sigma Aldrich, St. Louis, MO) was mixed with 1 g of polyvinylpyrrolidone (PVP) (Sigma Aldrich, St. Louis, MO) and dissolved in 30 mL of deionized water. Next, 1.5 mL of hydrazine hydrate (Sigma Aldrich, St. Louis, MO) and 3 mL of an ammonia ($NH_3$) (Sigma Aldrich, St. Louis, MO) solution (25% w/w) were added. The solution was stirred at room temperature and then transferred into a Teflon-lined stainless-steel reactor and placed into an oven at 180° C. for 4 hours. Right after the reaction, the mixture was allowed to cool down to room temperature.

For the green synthesis route, the process described by Lu et al. [39] was followed with modifications. Telluric acid ($H_2TeO_4$) (Sigma Aldrich, St. Louis, MO) was mixed with 0.15 g of a starch (Sigma Aldrich, St. Louis, MO) solution in deionized water. Then, the mixture was transferred into a Teflon-lined stainless-steel reactor and placed into an oven at 160° C. for 15 hours. After the reaction, the mixture was allowed to cool down at room temperature. Non-limiting examples of the chemical and green synthetic routes are shown in Equations 1 and 2 below.

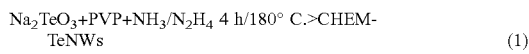

(1)

Equation 1. Reaction for the synthesis of TeNWs by chemical synthesis (1).

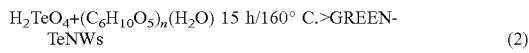

(2)

Equation 2. Reaction for the synthesis of TeNWs by green synthesis (2).

Once at room temperature, the final products from both synthesis methods were purified using the same protocol. The nanowire solutions were centrifuged at 10,000 rpm for 20 min, and the pellet was subsequently washed twice with water and centrifuged again using same speed and time. Finally, the precipitate was re-suspended in 35 mL of deionized water. The resulting solution containing the nanowires was transferred into a 20 mL glass vial, which was then placed in a freezer at −80° C. for 4 hours and lyophilized overnight. The final powder was weighed and re-suspended in a suitable amount of deionized and autoclaved water to reach the final concentration needed for further experiments.

The methods for hydrothermal synthesis of TeNWs using both chemical and green synthesis protocols are compared below in Table 4.

TABLE 4

Synthesis conditions of the protocols used to make TeNWs.

| Reaction features | CHEM-TeNWs | GREEN-TeNWs |
|---|---|---|
| Reducing agents | PVP/$NH_3$/$N_2H_4$ | Starch |
| Conditions | 180° C./4 hours | 160° C./15 hours |

One of the most remarkable differences between the two synthesis methods is the relative cost and quantity of the reducing agents needed to reduce ionic tellurium to elemental tellurium. While CHEM-TeNWs were generated in an aqueous solution in the presence of three reducing agents (PVP, hydrazine, and ammonia), the GREEN-TeNWs were reduced using only starch, which is both cheaper and much more environmentally friendly.

In the chemical synthesis, use of hydrazine and ammonia raises a huge safety concern when performing this process. Both reagents are flammable, extremely toxic, and hazardous. Hydrazine, in particular, produces explosive vapors/air mixtures at about 38° C. Besides, it is corrosive to metals and skin and a threat to the environment. Face shields and full-face respirators are needed to work with this chemical. PVP, however, is a water-soluble polymer that contributes to the formation of the nanostructures and is FDA approved.

On the other hand, the green synthetic approach only needs starch, which is a safe, naturally-occurring, reducing and stabilizing agent. This polymeric carbohydrate consists of a large number of glucose units that can reduce the tellurium ions to their elemental form. Therefore, because no additional agent is needed, this method holds advantages over the chemical synthesis method in both cost and safety. Another concern to note is the production of toxic by-products. While waste produced from CHEM-TeNWs synthesis should be considered hazardous, the generation of reaction-derived products from the green synthesis process developed should not be viewed as an environmental threat.

Regarding the time for the reactions, the chemical synthesis of TeNWs took 4 hours at 160° C. while the green process took 15 hours at 180° C. This extra reaction time is a result of the lower reducing power of starch relative to using hydrazine, ammonia, and PVP; however, taking into account the hazards of the chemicals and byproducts of the chemical synthesis approach, the green methodology still has several advantages such as being more economical, easy, and use of a straightforward hydrothermal synthesis method. Nevertheless, the green-synthetic approach employed can be made quicker since the time used for the growth of the nanowires can be reduced to a couple of hours.

Example 2

Analysis of Green Biogenic TeNWs and Chemical TeNWs

Morphological and Chemical Characterization

Morphological characterization was completed for both synthesis approaches with size and coating characteristics reported in Table 5

TABLE 5

Data from Transmission Electron Microscopy (TEM) for size and coating

| Structures | CHEM-TeNWs | GREEN-TeNWs |
|---|---|---|
| Length | Several microns | Several microns |
| Width | 32 ± 11 nm | 25 ± 8 nm |
| Coating | No | Yes |

Specifically, CHEM-TeNWs (FIGS. 1-2, 5-6) had an average diameter about 30 nm with a length of several micrometers. The wires showed a low degree of aggregation. On the other hand, GREEN-TeNWs (FIGS. 3-4, 7-8) showed an average diameter about 20 nm with similar length. Examining FIGS. 7-8 (SEM images), a peculiarity of these GREEN-TeNWs structures came from their morphology: nanowires started growing from a particular (central) point, and they extended as far as they could from this point. The wires started growing from a cluster and extended for several micrometers, with a star-shaped structure that was difficult to notice when the clusters were close to one another. The main trunk is divided into several smaller sections at the end of the structure as ramifications, which produced branches that grew alongside one another (see FIGS. 7-8). In the transmission electron microscopy (TEM) images of TeNWs, the CHEM-TeNWs with a low degree of aggregation were dispersed within the solution (FIGS. 1-2); GREEN-TeNWs (FIGS. 3-4) showed a higher degree of aggregation and the presence of an organic-coating was noticed.

Energy Dispersive X-Ray (EDX) measurements were completed for both the chemically and green-synthesized nanostructures. For CHEM-TeNWs (FIG. 9), EDX analysis showed that the electron-dense nanowires had specific tellurium absorption peaks. For GREEN-TeNWs, the EDX peaks for tellurium were higher due to the higher concentration of tellurium within the sample (FIG. 10). When the analysis of the GREEN-TeNWs focused on the surrounding (coated) areas of the nanostructures (see FIG. 11), the carbon peak was significantly raised compared with the measurement of the tellurium metallic core. This, aside from the absence of a tellurium peak, indicated an organic composition of the coating on the GREEN-TeNWs (FIG. 11).

Example 3

Anticancer and Cytotoxicity Measurements of GREEN-TeNWs and CHEM-TeNWs

In Vitro Cytotoxicity of TeNWs

In vitro cytotoxicity assays were performed with human dermal fibroblast (HDF) cells and melanoma cells (ATCC® CRL-1619™, Manassas, VA). Data from the nanowire treatment were compared with a control that contained just cells and media. Further comparison was made between HDF and melanoma cells with the aim to determine potential anticancer activity. Same experiments were performed using chemical and green-synthetized nanowires to determine the effect of the natural coating present on GREEN-TeNWs on the proliferation of the cells. Discussed below are MTS assays on human dermal fibroblasts (FIGS. 18-19) and melanoma (FIGS. 20-21) cells in the presence of chemically synthesized (FIGS. 18, 20) and green-synthesized (FIGS. 19, 21) Te nanowires at concentrations ranging from 5-100 µg/mL. N=3. Data is represented as mean±SD *$p<0.01$, **$p<0.005$. Note that in FIGS. 18-21, the 0 µg/mL concentration represents a control at Day 1, Day 3, and Day 5.

For HDF experiments, nanowires with a concentration between 5 and 100 µg/mL were tested. For CHEM-TeNWs, the same proliferation trend was observed within the 3rd and 5th day for concentrations up to 15 µg/mL compared to the control (FIG. 18). However, the number of cells were less than those for the control in all the cases. Larger concentrations showed degeneration of the cell proliferation. When GREEN-TeNWs were tested on the cells, a similar proliferation trend was observed for each of the concentrations (FIG. 19). An especially unusual behavior was shown at levels between 15 and 75 µg/mL, with a higher number of cells growing within the 3rd and the 5th day compared with the first 24 hours. From the comparison of both nanostructures, it can be concluded that the green-synthetized structures enhanced cell proliferation over a broader range of concentrations compared to the chemical synthetic ones.

The cytotoxic effect of tellurium nanostructures is the result of active physic-chemical interactions of elemental tellurium with the functional groups of intracellular proteins and the bases and phosphate groups in DNA [40]. While cytotoxicity was apparent for the CHEM-TeNWs (FIG. 18), it is believed that the enhanced biocompatibility in GREEN-TeNWs (FIG. 19) is most likely due to the presence of a natural, organic coating that encompasses the tellurium core. The presence of a carbon layer as the natural coating introduces a biodegradable material that can enhance cell proliferation.

When melanoma cells were treated with CHEM-TeNWs, cell proliferation showed a similar trend as that of the control at concentrations up to 25 µg/mL (FIG. 20). In FIG. 20, the 0 µg/mL concentration represents the control at Day 1 (far left bar), Day 3 (center bar), and Day 5 (far right bar). From 0-10 µg/mL, GREEN-TeNWs showed similar behavior (see FIG. 21). Nonetheless, levels between 10 and 100 µg/mL showed a delay in the cell proliferation compared to the control over the tested time-period. It has been hypothesized that TeNWs have the potential ability to slow down the signaling processes present in cancerous cells [41, 42]. Therefore, both synthesis methods produce nanostructures with anticancer properties; but, specifically, this behavior was particularly enhanced in the case of the GREEN-TeNWs.

Improved cytocompatibility and anticancer activity were observed for GREEN-TeNWs than CHEM-TeNWs. Not only were the GREEN-TeNWs produced with significantly less toxic materials, but their properties towards enhancing healthy cell proliferation and decreasing cancer cell proliferation were greater.

On the fifth day of the experiments, CHEM-TeNWs and GREEN-TeNWs were compared for cell biocompatibility using HDF cells (FIG. 22), and for cytotoxic effect using melanoma cells (FIG. 23) using data obtained from the MTS assays.

The low cytotoxicity for HDF cells can be appreciated especially at high concentrations of TeNWs, with a noticeable difference between CHEM-TeNWs, with higher cytotoxicity for HDF, and GREEN-TeNWs, which allow higher cell proliferation (FIG. 22). At low concentrations, between 5 and 15 µg/mL, the difference in terms of biocompatibility is almost inappreciable. The biggest difference was noticed at a concentration of 25 µg/mL.

For experiments with cancerous cells (FIG. 23), the opposite behavior was observed. GREEN-TeNWs did not allow the cell proliferation of melanoma cells at concentrations ranging between 15 and 100 µg/mL. As noted with HDF cells, the difference at the concentration of 25 µg/mL was large. From these data it can be concluded that at a GREEN-TeNWs concentration of 25 µg/mL, both maximum biocompatibility for HDF and the maximum cytotoxic effect for melanoma cells was achieved compared to CHEM-TeNWs used at the same concentration. In general, the behavior of GREEN-TeNWs after 5 days, in terms of low cytotoxicity for HDF and high cytotoxicity for melanoma cells, respectively, was enhanced in comparison with CHEM-TeNWs.

$IC_{50}$ values were calculated for all the experiments to obtain the minimum inhibitory concentration for both HDF and melanoma cells (see Table 6). This value was obtained after 5 days of experiments through measuring the potency of the nanowires to inhibit the normal biological functioning of the cells.

TABLE 6

IC$_{50}$ values for both CHEM- and GREEN-TeNWs in experimental assays with HDF and melanoma cells after 5 days of experiment.

| Cell assay | CHEM-TeNWs | GREEN-TeNWs |
| --- | --- | --- |
| HDF | 60.22 ± 15.25 μg/mL | 70.05 ± 10.58 μg/mL |
| Melanoma | 63.14 ± 6.078 μg/mL | 16.46 ± 1.96 μg/mL |

Example 4

Instruments, Materials, and Methods

Instruments and Materials

A Heratherm™ General Protocol Oven (Thermo Scientific™) was used to produce the hydrothermal reaction for both chemical and green methodologies. An Eppendorf™ Model 5804-R Centrifuge was used for the centrifugation of samples. A FreeZone Plus 2.5 Liter Cascade Console Freeze Dry System was used to purify the samples and obtain the final tellurium nanowire structures.

TeNWs prepared by both chemical synthetic and green approaches were properly characterized via a JEM-1010 transmission electron microscope (TEM) (JEOL USA Inc., Peabody, MA). For sample preparation, purified nanostructures were air-dried on 300-mesh copper-coated carbon grids (Electron Microscopy Sciences, Hatfield, PA). The samples were then imaged up to an 80,000× magnification with an accelerating voltage of 80.0 kV.

Energy dispersive X-ray spectroscopy analysis was performed using a dedicated EDS detector coupled with a Hitachi S-4800 SEM. TeNW samples were affixed to 300-mesh copper-coated carbon grids and placed into an aluminum pin mount. An accelerating voltage of 10.0 kV was used to obtain an elemental spectrum for the nanowires.

FT-IR spectra were recorded using a PerkinElmer Spectrum 400 FT-IR/FT-near infrared in attenuated total reflectance (ATR) mode. For FT-IR spectroscopy measurements, 5 μg of the dried sample was used for ATR.

Powder XRD patterns were obtained using a Rigaku Miniflex 600 (Rigaku Co., Tokyo, Japan) operating at a voltage of 40 kV, a current of 15 mA, and a Cu-Kα radiation of 1.542 Å. All XRD patterns were recorded at a room temperature with a step width of 0.05 (2) and a scan speed of 0.2°/min. The samples used were from the powder obtained after the purification process.

In the XPS, drops of both compounds dispersed in water were deposited on clean copper substrates for sample preparation. After water evaporation, the samples were loaded in a vacuum load lock chamber and then transferred to the XPS ultra-high vacuum chamber with a base pressure of $10^{-10}$ millibar. The XPS chamber is equipped with a hemispherical electron energy analyzer (SPECS Phoibos 100 spectrometer, Berlin, Germany) and an Mg-Kα (1,253.6 eV) X-ray source. The angle between the hemispherical analyzer and the plane of the surface was kept at 60°. Wide scan spectra were recorded using an energy step of 0.5 eV and a pass energy of 40 eV, while specific core level spectra (Te 3d, O 1s, and C 1s) were recorded using an energy step of 0.1 eV and a pass energy of 20 eV. The absolute binding energies of the photoelectron spectra were determined by referencing to the Te 3d 5/2 metallic core level at 573 eV. Data processing was performed with CasaXPS software (Casa software Ltd., Cheshire, UK). The contributions of the Mg-Kα satellite lines were subtracted.

Optical microscopy analysis was done on a phase contrast mode using an Axio Observer Z1 Inverted Fluorescence Microscope (Carl Zeiss, Oberkochen, Germany). For sample preparation, cells were grown on a 6-well plate with the presence of different concentrations of GREEN-TeNWs and CHEM-TeNWs for 1, 3, and 5 days. Images were taken at these time points.

In Vitro Cytotoxicity Assays with TeNWs

Cytotoxicity assays were performed with primary human dermal fibroblast cells (Lonza, CC-2509, AMP) and human melanoma cells (ATCC® CRL-1619™, Manassas, VA). The cells were cultured in Dulbecco's Modified Eagle Medium (DMEM; Thermo Fisher Scientific, Waltham, MA), supplemented with 10% fetal bovine serum (FBS; ATCC® 30-2020™, American Type Culture Collection, Manassas, VA) and 1% penicillin/streptomycin (Thermo Fisher Scientific, Waltham, MA). MTS assays (CellTiter 96® AQueous One Solution Cell Proliferation Assay Promega, Madison, WI) were carried out to assess cytotoxicity. Cells were seeded onto tissue-culture-treated 96-well plates (Thermo Fisher Scientific, Waltham, MA) at a final concentration of 5000 cells per well in 100 μL of cell culture medium. An incubation period of 24 hours at 37° C. in a humidified incubator with 5% carbon dioxide ($CO_2$) was employed. The culture medium was then replaced with 100 μL of fresh cell culture medium containing concentrations from 5 to 100 μg/mL of either CHEM-TeNWs or GREEN-TeNWs.

The cells were cultured for three different periods of time to compare the effects of the nanostructures on the cells after the first, third and fifth day following exposure. The cells were washed with PBS, and the original media was replaced with 100 μL of the MTS solution (prepared using a mixing ratio of 1:5 of MTS:Medium). After the addition of the solution, the 96-well plate was incubated for 4 hours in the incubator to allow for a color change. Then, the absorbance was measured at 490 nm on an absorbance plate reader (SpectraMAX M3, Molecular Devices) for cell viability after exposure to the TeNWs. Cell viability was calculated by dividing the average absorbance obtained for each sample by that of the control sample and then multiplied by 100. Controls containing cells and media, just media and nanowires in media, were also included in the 96-well plate to identify the healthy growth of cells without nanowires and determine the absorbance of both the media and the nanowires.

Statistical Analysis

All experiments were repeated in triplicate (N=3) to ensure reliability of the results. Statistical significance was assessed using Student's t-test, with $p<0.05$ being statistically significant. Results are displayed as mean±standard deviation.

As used herein, the term "about" and "approximately" are defined to be within 10%, 5%, 1%, or 0.5%.

As used herein, "consisting essentially of" allows the inclusion of materials or steps that do not materially affect the basic and novel characteristics of the claim. Any recitation herein of the term "comprising", particularly in a description of components of a composition or in a description of elements of a device, can be exchanged with the alternative expressions "consisting essentially of" or "consisting of".

REFERENCES

1. North, Emily J, and Rolf U Halden. "Plastics and Environmental Health: The Road Ahead." *Reviews on environmental health* 28.1 (2013): 1-8.

2. Bijlsma, Nicole, and Marc M Cohen. "Environmental Chemical Assessment in Clinical Practice: Unveiling the Elephant in the Room." *International journal of environmental research and public health* 13.2 (2016): 181.
3. Lopez, Joseph B et al. "Reducing the Environmental Impact of Clinical Laboratories." *The Clinical biochemist. Reviews* 38.1 (2017): 3-11.
4. Wang, Linlin, Chen Hu, and Longquan Shao. "The Antimicrobial Activity of Nanoparticles: Present Situation and Prospects for the Future." *International Journal of Nanomedicine* Volume 12 (2017): 1227-1249.
5. Hemeg, Hassan. "Nanomaterials for Alternative Antibacterial Therapy." *International Journal of Nanomedicine* Volume 12 (2017): 8211-8225.
6. Graves, Joseph L et al. "Antimicrobial Nanomaterials: Why Evolution Matters." *Nanomaterials* (Basel, Switzerland) 7.10 (2017): n. pag.
7. Jain, S, D G Hirst, and J M O'Sullivan. "Gold Nanoparticles as Novel Agents for Cancer Therapy." *The British Journal of Radiology* 85.1010 (2012): 101-113.
8. Cai, Weibo et al. "Applications of Gold Nanoparticles in Cancer Nanotechnology." *Nanotechnology, science and applications* 1 (2008): 17-32.
9. Nune, Satish K et al. "Nanoparticles for Biomedical Imaging." *Expert Opinion on Drug Delivery* 6.11 (2009): 1175-1194.
10. Estelrich, Joan, Maria Jesus Sanchez-Martin, and Maria Antonia Busquets. "Nanoparticles in Magnetic Resonance Imaging: From Simple to Dual Contrast Agents." *International journal of nanomedicine* 10 (2015): 1727-41.
11. Choi, Hak Soo, and John V Frangioni. "Nanoparticles for Biomedical Imaging: Fundamentals of Clinical Translation." *Molecular imaging* 9.6 (2010): 291-310.
12. Park, Kinam. "Facing the Truth about Nanotechnology in Drug Delivery." *ACS Nano* 7.9 (2013): 7442-7447.
13. De Jong, Wim H, and Paul J A Borm. "Drug Delivery and Nanoparticles: applications and Hazards." *International journal of nanomedicine* 3.2 (2008): 133-49.
14. Wang, Yi-Feng et al. "Nanoparticle-Based Drug Delivery Systems: What Can They Really Do in Vivo?" *F1000Research* 6 (2017): 681.
15. Kogler, Martin et al. "Bare Laser-Synthesized Au-Based Nanoparticles as Nondisturbing Surface-Enhanced Raman Scattering Probes for Bacteria Identification." *Journal of Biophotonics* (2018): e201700225.
16. Fernandez-Bravo, Angel et al. "Femtosecond Laser Ablation Synthesis of Aryl Functional Group Substituted Gold Nanoparticles." *Journal of nanoscience and nanotechnology* 17.4 (2017): 2852-856.
17. Bukhtiar, Arfan, and Zou BingSuo. "The Preparation and Optical Properties of Ni(II) and Mn(II) Doped in ZnTe Nanobelt/Nanorod by Using Chemical Vapor Deposition." *Journal of Nanoscience and Nanotechnology* 18.7 (2018): 4700-4713.
18. Islam, Mohammad et al. "Metal/Carbon Hybrid Nanostructures Produced from Plasma-Enhanced Chemical Vapor Deposition over Nafion-Supported Electrochemically Deposited Cobalt Nanoparticles." *Materials* 11.5 (2018): 687.
19. Kulkarni, Narendra, and Uday Muddapur. "Biosynthesis of Metal Nanoparticles: A Review." *Journal of Nanotechnology* 2014 (2014): 1-8.
20. Ai, Jafar et al. "Nanotoxicology and Nanoparticle Safety in Biomedical Designs." *International journal of nanomedicine* 6 (2011): 1117-27.
21. Shah, Monaliben et al. "Green Synthesis of Metallic Nanoparticles via Biological Entities." *Materials* 8.11 (2015): 7278-7308.
22. Riehemann, Kristina et al. "Nanomedicine-Challenge and Perspectives." *Angewandte Chemie International Edition* 48.5 (2009): 872-897.
23. Hussain, Imtiyaz et al. "Green Synthesis of Nanoparticles and Its Potential Application." *Biotechnology Letters* 38.4 (2016): 545-560.
24. Medina Cruz, David, Gujie Mi, and Thomas J. Webster. "Synthesis and Characterization of Biogenic Selenium Nanoparticles with Antimicrobial Properties Made by *Staphylococcus Aureus*, Methicillin-Resistant *Staphylococcus Aureus* (MRSA), *Escherichia Coli*, and *Pseudomonas Aeruginosa*." *Journal of Biomedical Materials Research Part A* 106.5 (2018): 1400-1412.
25. Larios-Rodriguez, E et al. "Bio-Synthesis of Gold Nanoparticles by Human Epithelial Cells, in Vivo." *Nanotechnology* 22.35 (2011): 355601.
26. El-Said, Waleed A. et al. "Synthesis of Metal Nanoparticles Inside Living Human Cells Based on the Intracellular Formation Process." *Advanced Materials* 26.6 (2014): 910-918.
27. Molnar, Zsofia et al. "Green Synthesis of Gold Nanoparticles by Thermophilic Filamentous Fungi." *Scientific Reports* 8.1 (2018): 3943.
28. Makarov, V V et al. "'Green' Nanotechnologies: Synthesis of Metal Nanoparticles Using Plants." *Acta naturae* 6.1 (2014): 35-44.
29. Singh, Priyanka et al. "Biological Synthesis of Nanoparticles from Plants and Microorganisms." *Trends in Biotechnology* 34.7 (2016): 588-599.
30. Dhand, Vivek et al. "Green Synthesis of Silver Nanoparticles Using Coffea Arabica Seed Extract and Its Antibacterial Activity." *Materials Science and Engineering: C* 58 (2016): 36-43.
31. Wu, Lina et al. "A Green Synthesis of Carbon Nanoparticles from Honey and Their Use in Real-Time Photoacoustic Imaging." *Nano Research* 6.5 (2013): 312-325.
32. Surendra, T. V. et al. "Vegetable Peel Waste for the Production of ZnO Nanoparticles and Its Toxicological Efficiency, Antifungal, Hemolytic, and Antibacterial Activities." *Nanoscale Research Letters* 11.1 (2016): 546.
33. Gurunathan, Sangiliyandi et al. "A Green Chemistry Approach for Synthesizing Biocompatible Gold Nanoparticles." *Nanoscale Research Letters* 9.1 (2014): 248.
34. Mukherjee, Sudip et al. "Green Chemistry Approach for the Synthesis and Stabilization of Biocompatible Gold Nanoparticles and Their Potential Applications in Cancer Therapy." *Nanotechnology* 23.45 (2012): 455103.
35. Rehana, Dilaveez et al. "Evaluation of Antioxidant and Anticancer Activity of Copper Oxide Nanoparticles Synthesized Using Medicinally Important Plant Extracts." *Biomedicine & Pharmacotherapy* 89 (2017): 1067-1077.
36. Kelkawi, Ali Hamad Abd, Abolghasem Abbasi Kajani, and Abdol-Khalegh Bordbar. "Green Synthesis of Silver Nanoparticles Using Mentha Pulegium and Investigation of Their Antibacterial, Antifungal and Anticancer Activity." *IET Nanobiotechnology* 11.4 (2017): 370-376.
37. Sudhasree, S. et al. "Synthesis of Nickel Nanoparticles by Chemical and Green Route and Their Comparison in Respect to Biological Effect and Toxicity." *Toxicological & Environmental Chemistry* 96.5 (2014): 743-754.
38. Hong, Wei, Jin Wang, and Erkang Wang. "Facile Synthesis of PdAgTe Nanowires with Superior Electrocatalytic Activity." *Journal of Power Sources* 272 (2014): 940-945.

39. Lu, Qingyi, Feng Gao, and Sridhar Komarneni. "A Green Chemical Approach to the Synthesis of Tellurium Nanowires." *Langmuir* 21.13 (2005): 6002-6005.
40. Sredni, Benjamin. "Immunomodulating Tellurium Compounds as Anti-Cancer Agents." *Seminars in Cancer Biology* 22.1 (2012): 60-69.
41. Yang, Darren, and Wesley P Wong. "Small but Mighty: Nanoparticles Probe Cellular Signaling Pathways." *Developmental cell* 37.5 (2016): 397-8.
42. Marano, Francelyne et al. "Nanoparticles: Molecular Targets and Cell Signalling." *Archives of Toxicology* 85.7 (2011): 733-741.

The invention claimed is:

1. Coated tellurium nano wires having a core comprising tellurium and an outer coating comprising a polymer, wherein the polymer is starch, and wherein the coated tellurium nanowires are produced by a method comprising the steps of:
   (a) heating an aqueous solution or suspension comprising telluric acid ($H_2TeO_4$) and starch in a sealed vessel at a temperature from about 120° C. to about 200° C. for about 2 hours to about 20 hours;
   (b) centrifuging the product from step (a) to obtain a pellet;
   (c) resuspending the pellet in an aqueous solution; and
   (d) lyophilizing the resuspended pellet resulting from (c), whereby the coated tellurium nanowires are produced; and wherein at least a portion of the produced coated tellurium nano wires form a star-shaped structure comprising coated tellurium nanowires radiating outwards from a central point.

2. The coated tellurium nanowires of claim 1, wherein the coated tellurium nanowires do not comprise amorphous tellurium.

3. The coated tellurium nanowires of claim 1, wherein the core comprises tellurium hexagonal crystal structure.

4. The coated tellurium nanowires of claim 1, wherein the core consists essentially of tellurium hexagonal crystal structure.

5. The coated tellurium nanowires of claim 1, wherein proliferation of cancer cells is inhibited at least twice as much as proliferation of non-cancerous cells is inhibited when the coated tellurium nanowires are administered to a subject having cancer.

6. The coated tellurium nanowires of claim 1, wherein the coated tellurium nanowires have a diameter of about 15 nm to about 35 nm.

7. The coated tellurium nanowires of claim 1, wherein the coated tellurium nanowires have a coating that is at least 1 nm thick.

* * * * *